(12) United States Patent
Reed et al.

(10) Patent No.: US 6,638,734 B1
(45) Date of Patent: Oct. 28, 2003

(54) NUCLEIC ACID ENCODING PROTEINS INVOLVED IN PROTEIN DEGRADATION, PRODUCTS AND METHODS RELATED THERETO

(75) Inventors: John C. Reed, Rancho Santa Fe, CA (US); Shu-ichi Matsuzawa, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 49 days.

(21) Appl. No.: 09/591,694

(22) Filed: Jun. 9, 2000

Related U.S. Application Data
(60) Provisional application No. 60/367,334, filed on Jun. 11, 1999.

(51) Int. Cl.$^7$ .............................. C12P 2/06; C07K 14/00
(52) U.S. Cl. ........................ 435/69.1; 530/350; 530/300
(58) Field of Search ................ 435/7.1, 69.1; 530/350, 300

(56) References Cited

U.S. PATENT DOCUMENTS 5,851,791 A * 12/1998 Vierstra et al. .......... 435/168.1

FOREIGN PATENT DOCUMENTS

| WO | WO 9722695 | 6/1997 |
| WO | WO 9841624 | 9/1998 |
| WO | WO 9842741 | 10/1998 |
| WO | WO 9918989 | 4/1999 |
| WO | WO 9946374 | 9/1999 |
| WO | WO 9947540 | 9/1999 |

OTHER PUBLICATIONS

Cenciarelli et al., "Identification of a family of human F–box proteins," *Current Biology* 9(20):1177–1179 (1999).
Filipek and Kuźnicki, "Molecular cloning and expression of a mouse brain cDNA encoding a novel protein target of calcylin," *Journal of Neuorchemistry* 70(5):1793–1798 (1998).
Hu and Fearon, "Siah–1 N–terminal Ring domain is required for proteolysis function, and C–terminal sequences regulate oligomerization and binding to target proteins," *Molecular and Cellular Biology* 19(1):724–732 (1999).
EMBL Database Accession No. AL035305.
EMBL Database Accession No. 075986.
EMBL Database Accession No. Q9UKT2.
EMBL Database Accession No. Q9UKT4.
EMBL Database Accession No. Q9UK97.
EMBL Database Accession No. Q9Y3I1.
EMBL Database Accession No. Q9Y593.
Altschul et al., "Gapped Blast and PSI–Blast: A New Generation of Protein Database Search Programs," *Nucleic Acids Res.* 25:3389–3402 (1997).

Amson et al., "Isolation of 10 Differentially Expressed cDNAs in P53–induced Apoptosis: Activation of the Vertebrate Homologue of the Drosophila Seven in Absentia Gene," *PNAS, USA,* 93:3953–3957 (1996).
Ciechanover, A., "The Ubiquitin–proteasome Pathway: on Protein Death and Cell Life," *EMBO J.,* 17(24):7151–7160 (1998).
Cohen et al., "An Artificial Cell–cycle Inhibitor Isolated from a Combinatorial Library," *Proc. Natl. Acad. Sci.,* 95:14272 (1998).
Colas et al., "Genetic Selection of Peptide Aptamers That Recognize and Inhibit Cyclin–dependent Kinase 2," *Nature,* 380:548 (1996).
Fabbrizio et al., "Inhibition of mammalian cell proliferation by genetically selected peptide aptamers that functionally antagonize E2F activity," *Oncogene,* 18:4357 (1999).
Fearon et al., "Identification of a Chromosome 18q Gene That Is Altered in Colorectal Cancers," *Science,* 247:49–56 (1990).
Geyer et al., "'Mutagenesis' by Peptide Aptamers Identifies Genetic Network Members and Pathway Connections," *Proc. Natl. Acad. Sci.,* 96:8567 (1999).
GenBank Accession No.: AA054272—zf54c01.s1 Soares retina N2b4HR Homo sapiens cDNA clone Image:380736 3' similar to TR:G297035 G297035 SIAH–1A Protein; mRNA sequence.
GenBank Accession No.: AA258606—zr60c05.s1 Soares_NhHMPu_S1 Homo sapiens cDNA clone Image:667784 3' similar to TR:G297035 G297035 SIAH–1A Protein; mRNA sequence.
GenBank Accession No.: AA923663—oh08e09.s1 NCI_CGAP_Co8 Homo sapiens cDNA clone Image:1457224 3' similar to TR:Q92880 Q92880 Seven in Absentia Homolog.; mRNA sequence.
GenBank Accession No.: AA418482—zv93b08.s1 Soares_NhHMPu_S1 Homo sapiens cDNA clone Image:767319 3' similar to TR:G297035 G297035 SIAH–1A Protein; mRNA sequence.
GenBank Accession No.: AI167464—ox68a08.s1 Soares_NhHMPu_S1 Homo sapiens cDNA clone Image:1661462 3' similar to TR:Q92880 Q92880 Seven in Absentia Homolog.; mRNA sequence.

(List continued on next page.)

*Primary Examiner*—Karen Cochrane Carlson
(74) *Attorney, Agent, or Firm*—McDermott, Will & Emery

(57) ABSTRACT

In accordance with the present invention, there are provided novel Siah-Mediated-Degradation-Proteins (SMDPs) and/or SCF-Complex Proteins (SCPs). Nucleic acid sequences encoding such proteins and assays employing same are also disclosed. The invention SMDPs and/or SCPs can be employed in a variety of ways, for example, for the production of anti-SMDP and/or SCP antibodies thereto, in therapeutic compositions, and methods employing such proteins and/or antibodies for drug screening, functional genomics and other applications. Also provided are transgenic non-human mammals that express the invention protein.

7 Claims, 5 Drawing Sheets

OTHER PUBLICATIONS

GenBank Accession No.: AL031178—Human DNA sequence from clone 341E18 on chromosome 6p11.2–12.3. Contains a Serine/Threonine Protein Kinase gene (presumptive isolog of a Rat gene) and a novel alternatively spliced gene. Contains a putative CpG island, ESTs and GSSs, complete sequence.

Huibregtse et al., "A Family of Proteins Structurally and Functionally Related to the E6–AP Ubiquitin–Protein Ligase," *Proc. Natl. Acad. Sci. USA,* 92:2563–2567 (1995).

Hu et al., "Characterization of Human Homologs of the Drosophila Seven in Absentia (Sina) Gene," *Genomics,* 46:103–111 (1997).

Kamura et al., "The Elongin BC Complex Interacts with the Conserved Socs–box Motif Present in Members of the SOCS, ras, WD–40 Repeat, and Ankyrin Repeat Families," *Genes Dev.,* 12:3872–81 (1998).

Kinzler et al., "Lessons from hereditary Colorectal Cancer," *Cell,* 87(2):159–170 (1996).

Korinek et al., "Constitutive Transcriptional Activation by a Beta–catenin–Tcf Complex in APC–/–Colon Carcinoma," *Science,* 275:1784–1787 (1997).

Latres et al., "The Human F Box Protein Beta–trcp Associates with the Cull/skp1 Complex and Regulates the Stability of Beta–catenin," *Oncogene,* 18:849–854 (1999).

Li et al., "Photoreceptor Cell Differentiation Requires Regulated Proteolysis of the Transcriptional Repressor Tramtrack," *Cell,* 469–478 (1997).

Matsuzawa et al., "P53–inducible Human Homologue of Drosophila Seven in Absentia (Siah) Inhibits Cell Growth: Suppression by BAG–1," *EMBO J.,* 17(1):2736–2747 (1998).

Morin et al., "Activation of β–Catenin–Tcf Signaling in Colon Cancer by Mutations in β–Catenin or APC," *Science,* 275:1787–1790 (1997).

Nemani et al., "Activation of the Human Homologue of the Drosophila Sina Gene in Apoptosis and Tumor Suppression," *Proc. Natl. Sci. USA,* 93:9039–9042 (1996).

Patton et al., "Combinatorial Control in Ubiquitin–dependent Proteolysis: Don't Skp the F–Box Hypothesis," *TIG,* 14(6):236–243 (1998).

Rubinfeld et al., "Stabilization of b–Catenin by Genetic Defectsin Melanoma Cell Lines," *Science,* 275:1790–1792 (1997).

Starr and Hilton, "Negative Regulation of the JAK/STAT Pathway," *Bioessays,* 21:47–52 (1999).

Takayama et al., "Cloning and Functional Analysis of Bag–1: a Novel Bcl–2–binding Protein with Anti–cell Death Activity," *Cell,* 80(2):279–284 (1995).

Tang et al., "PHYL Acts to Down–regulate $TTK_{88}$, a Transcriptional Repressor of Neuronal Cell Fates, by a SINA–dependent Mechanism," *Cell,* 90:459–467 (1997).

Tyers and Willems, "One Ring to Rule a Superfamily of $E_3$ Ubiquitin Ligases," *Science,* 284:601–604 (1999).

Winston et al., "The $SCF^{b-TRCP}$–Ubiquitin Ligase Complex Associates Specifically with Phosphorylated Destruction Motifs in $I_kB_a$ and β–Catenin and Stimulates $I_kB_a$ Ubiquitination In Vitro," *Genes & Dev.,* 13:270–283 (1999).

Zhang et al., "p19Skp1 and p45Skp2 Are Essential Elements of the Cyclin A–cdk2 S Phase Kinase," *Cell,* 82(6):915–925 (1995).

\* cited by examiner

NUCLEIC ACID ENCODING PROTEINS INVOLVED IN PROTEIN DEGRADATION, PRODUCTS AND METHODS RELATED THERETO

This application claims the benefit of U.S. Provisional Application No. 60/367,334, filed Jun. 11, 1999, now abandoned, which was converted from U.S. Ser. No. 09/330,517, now abandoned and which is incorporated herein by reference.

Portions of the invention described herein were made in the course of research supported in part by NIH grant CA67329. The Government may have certain rights in this invention.

FIELD OF THE INVENTION

The present invention relates to nucleic acids and proteins encoded thereby.

BACKGROUND OF THE INVENTION

The temporal coordination of sequential steps within the eukaryotic cell cycle is governed in large part by protein degradation, involving targeted ubiquitination of specific cell cycle regulatory proteins followed by their destruction by the 26S proteasome (reviewed in Ciechanover, A. 1998, *EMBO J.*, 17(24):7151–7160). Among the cell cycle regulators whose levels are controlled by ubiquitination and subsequent proteosome-dependent degradation are the cyclins (cyclins A, B, C, D1, E) and several of the cyclin-dependent kinase (cdk) inhibitory proteins including p21-Waf1 and p27 Kip. Defects in this highly regulated process of protein turnover have been documented in many types of cancer.

The steps involved in polyubiquitination of specific proteins in cells involve the concerted actions of E1, E2, and E3-type enzymes. E1 proteins form thioester bonds in which the sulfhydryl group of internal cysteine residues binds the carboxyl amino acid of ubiquitin, thereby activating ubiquitin for subsequent transfer to E2-family proteins. E2 family proteins then transfer activated ubiquitin to the free amino-groups of lysine side chains in target proteins directly. More often, however, E2-family proteins collaborate with E3 proteins which bind particular target proteins and orchestrate their interactions with E2s, coordinating the polyubiquitination of these target proteins in highly regulated manners Ciechanover, A. 1998 supra. E3 functions are sometimes embodied in multiprotein complexes rather than mediated by a single protein.

The ubiquitination and degradation of a variety of cyclins, cyclin-dependent kinases (cdks) and cdk-inhibitors is temporally controlled during the cell cycle by SFC complexes. Theses multiprotein complexes function as E3-like entities, and contain the Skp-1 protein, at least one Cullin-family protein, and at least one F-box protein, thus the acronym SCF: S=Skp1; C=Cullin; F=F-box) (reviewed in Patton, E. E. et al., 1998, *TIG* 14(6):236–243). F-box proteins contain a conserved motif, the F-box, which mediates their interactions with Skp-1. The F-box proteins also contain other domains which allow them to simultaneously bind specific substrate proteins, which are then targeted for degradation via polyubiquitination. One such F-box protein identified in humans is b-Trcp, which forms a SCF complex with Skp-1 and Cul-1, and which interacts with β-catenin, targeting it for degradation (Latres, et al., 1999, *Oncogene*, 18:849–854, and Winston, J. J. et al., 1999, *Genes & Dev.*, 13:270–283).

Siah-family proteins represent mammalian homologs of the Drosophila Sina protein. Sina is required for R7 photoreceptor cell differentiation within the sevenless pathway. Sina binds a ubiquitin-conjugating enzyme (E2) via an N-terminal RING domain. Heterocomplexes of Sina and another protein called Phyllopodia form a E3-complex which interacts with a transcriptional repressor called Tramtrack, targeting it for polyubiqitination and proteosome-mediated degradation in the fly (Tang, A. H. et al., 1997, *Cell*, 90:459–467 and Li, S. et al., 1997, *Cell*, 469–478). The destruction of Tramtrack is necessary for differentiation of R7 cells.

At present, little is known about the expression of mammalian genes related to the Siah-mediated-protein-degradation family of proteins in normal cells and cancers. Moreover, the diversity of functions of the Siah-mediated-protein-degradation family proteins remain unclear. Therefore, there continues to be a need in the art for the discovery of additional proteins that interact with the Siah-mediated-protein-degradation pathway, such as proteins that bind Siah in vivo, and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Similarly, a need exists to identify additional components of SCF complexes which may operate in concert with or independently of Siah. The present invention satisfies these needs and provides related advantages as well.

BRIEF DESCRIPTION OF THE INVENTION

In accordance with the present invention, there are provided novel isolated nucleic acids encoding a variety of Siah-Mediated-Degradation-Proteins (SMDPs) involved in the Siah-mediated protein degradation pathways and/or SCF-Complex-Proteins (SCPs) involved in SCF-mediated protein degradation pathways. Further provided are vectors containing invention nucleic acids, probes that hybridize thereto, host cells transformed therewith, antisense-nucleic acids thereto and related compositions. The nucleic acid molecules described herein can be incorporated into a variety of expression systems known to those of skill in the art. In addition, the nucleic acid molecules of the present invention are useful as probes for assaying for the presence and/or amount of a SMDP and/or SCP gene or mRNA transcript in a given sample. The nucleic acid molecules described herein, and oligonucleotide fragments thereof, are also useful as primers and/or templates in a PCR reaction for amplifying genes encoding SMDP and/or SCP proteins.

In accordance with the present invention, there are also provided isolated mammalian SMDP and/or SCP proteins. These proteins, or fragments thereof, are useful in bioassays, as immunogens for producing anti-SMDP and/or SCP antibodies, or in therapeutic compositions containing such proteins and/or antibodies. Also provided are transgenic non-human mammals that express, or fail to express (e.g., knock-out), the invention protein.

Antibodies that are immunoreactive with invention SMDP and/or SCP proteins are also provided. These antibodies are useful in diagnostic assays to determine levels of SMDP and/or SCP proteins present in a given sample, e.g., tissue samples, Western blots, and the like. The antibodies can also be used to purify SMDP and/or SCP proteins from crude cell extracts and the like. Moreover, these antibodies are considered therapeutically useful to modulate the biological effect of SMDP and/or SCP proteins in vivo.

Also provided are bioassays for identifying compounds that modulate the activity of invention SMDP and/or SCP proteins. Methods and diagnostic systems for determining the levels of SMDP and/or SCP protein in various tissue samples are also provided. These diagnostic methods can be used for monitoring the level of therapeutically administered SMDP and/or SCP or fragments thereof to facilitate the maintenance of therapeutically effective amounts. These diagnostic methods can also be used to diagnose physiological disorders that result from abnormal levels of SMDP and/or SCP.

Also provided are systems using invention SMDPs, SCPs, or functional fragments thereof, for targeting any desired protein for ubiquitination and degradation, thus enabling novel gene discovery through functional genomics strategies or providing the basis for ablating target proteins involved in diseases for therapeutic purposes.

DETAILED DESCRIPTION OF THE INVENTION

Figures 1, 2, 3:
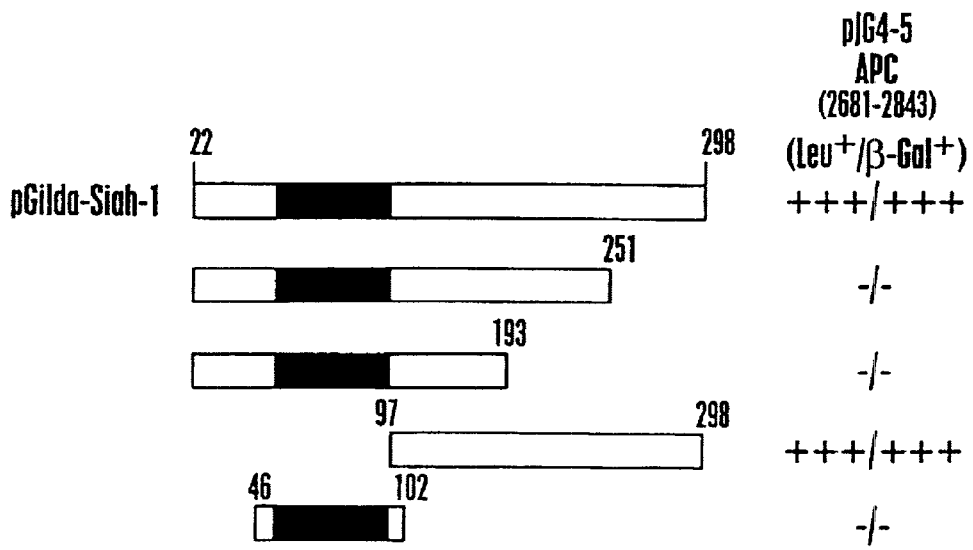
FIG. 1 shows an amino acid sequence comparison of SIP-L (SEQ ID NO:4) and SIP-S (SEQ ID NO:6).
FIG. 2 shows the Destruction-box amino acid consensus sequence of SAD.
FIG. 3 shows the Mapping of Siah-APC interaction domains as described in Example 12.

In accordance with the present invention, there are provided isolated nucleic acids, which encode novel mammalian Siah-Mediated-Degradation-Proteins (SMDPs) and/or SCF-Complex-Proteins (SCPs), and functional fragments thereof. SMDPs are involved in the Siah-mediated protein degradation pathways and SCPs are involved in SCF-mediated protein degradation pathways. In some instances, these two pathways for protein degradation may operate in collaboration, particularly in cases where proteins have been identified that physically link SMDPs to SCPs. Invention SMDPs and/or SCPs are contemplated herein to regulate protein degradation, either by activating or inhibiting such protein degradation.

As used herein, invention SMDPs are proteins that participate in the Siah-mediated protein degradation pathway. The term "Siah" refers to the mammalian family of proteins encoded by at least two genes referred to as SIAH1 and SIAH2 (Hu, G. et al., 1997, *Genomics*, 46:103–111). Like their Drosophila counterpart protein Sina, the Siah-1 and Siah-2 proteins bind ubiquitin conjugating enzymes (UBCs) via an N-terminal RING domain and target other proteins for degradation.

As used herein, invention SCPs are proteins that participate in the Skp-1, Cullin, F-box (SCF) protein degradation pathway. These proteins can be components of SCF complexes or proteins that associate with SCF complexes. In some instances an invention protein may fulfill the requirements of both a SMDP and a SCP.

Using yeast two-hybrid screening methods, targets of Siah-mediated protein degradation have been identified demonstrating the involvement of Siah and other inventions SMDPs and/or SCPs in pathways involved in cell growth regulation in cancers. For example, evidence is provided herein demonstrating that Siah-1 interacts indirectly with SCF complexes through associations with an invention SIP protein. Siah-1 has also been found to be an important regulator of cell growth, through its effects on ubiquitination and degradation of β-catenin and possibly other target proteins including an invention protein SAD.

Thus far, the only reported target of Siah-mediated degradation is DCC (Hu, G. et al., 1997, *Genes & Dev.*, 11:2701–2714), a putative tumor suppressor protein encoded by a gene which is commonly disrupted in colon cancers (Fearon, E. R. et al., 1990, *Science*, 247:49–56). The involvement of DCC in colon cancers however has recently been questioned, and it appears that a different gene located near DCC on 18q21 is the primary target of deletions in this chromosomal region (Fearon, E. R. et al., 1990, supra). However, the DCC protein has recently been shown to deliver either pro-apoptotic or anti-apoptotic signals, depending on whether it is complexed with its ligand Netrin. These observations suggest that deletion or inactivation of DCC could potentially contribute to tumorigensis by removing a pro-apoptotic influence from cells.

Another connection between the Siah-family of proteins and tumor suppressor genes has been found for p53. For example, the Siah-1 gene of mice was found among a group of immediate-early genes induced by p53 using a hemopoietic cell line as a model for p53-induced cell cycle arrest and apoptosis (Amson, R. B. et al., 1996, *PNAS, USA*, 93:3953–3957). Expression of Siah-1 was also indirectly correlated with increased apoptosis in tumor xenograph experiments, suggesting that Siah-1 could function as a tumor suppressor in some contexts (Nemani, M. et al., 1996, *Proc. Natl. Sci. USA* 93:9039–9042).

It has also been found that Siah-1 over-expression can induce cell cycle arrest independently of apoptosis in epithelial cancer cells (Matsuzawa, et al., 1998, *EMBO J.*, 17(10):2736–2747). Moreover, UV-irradiation at subapoptotic doses was shown to induce Siah-1 gene expression in MCF7 breast cancer cells and to promote cell cycle arrest. These and other data have implicated Siah-1 in a p53-inducible pathway for cell cycle arrest which runs parallel to the well-studied p21-Waf1 pathway (Matsuzawa, et al. 1998, supra).

The phrase "SMDP and/or SCP" refers to substantially pure native SMDP and/or SCP, or recombinantly produced proteins, including naturally occurring allelic variants thereof encoded by mRNA generated by alternative splicing of a primary transcript, and further including fragments thereof which retain at least one native biological activity, such as immunogenicity, the ability to bind to a SMDP and/or SCP, and the like. Exemplary SMDPs and/or SCPs referred to herein include amino acid sequences set forth in SEQ ID Nos:2 (Siah-1α), 4 (SIP-L), 6 (SIP-S), 8 (SAF-1α), 10 (SAF-1β), 12 (SAF-2) and 14 (SAD). Invention isolated SMDPs and/or SCPs are substantially pure and free of cellular components and/or contaminants normally associated with a native in vivo environment.

As used herein, the term "Siah-1α" refers to a splice-variant member of the mammalian, preferably human, Siah-family of proteins. The invention Siah-1α protein, or functional fragment thereof, is characterized by having the ability to bind to at least one or more of the proteins selected from APC (Kinzler K. W., et al., 1996, Cell, 87(2):159–170); BAG-1 (Takayama et al., 1995, Cell, 80(2):279–284); SIP-L; SIP-S; or other Siah proteins, such as Siah-1. Thus, homodimers of Siah-1α are contemplated herin. Invention Siah-1α proteins differ from Siah-1β (set forth as SIAH-1 in Hu et al., 1997, Genomics, 46:103–111) by containing an additional 16 amino acids at the amino-terminus. Thus, preferred invention Siah-1α proteins, and fragments thereof, comprise at least a portion of the 16 N-terminal amino acids of SEQ ID NO:2. A particularly preferred Siah-1α protein is set forth in SEQ ID NO:2.

In accordance with another embodiment of the invention, Siah-1 has been found to interact with an invention protein referred to herein as the "SIP" family. As used herein, the term "SIP" refers to any species, preferably mammalian, more preferably human, Siah-1-Interacting Protein (SIP). The invention SIP proteins, or functional fragments thereof, are characterized by having the ability to bind to at least one or more of the proteins selected from Siah-1, Skp1, or other SIP proteins. Thus, homodimers of invention SIP proteins are contemplated herein. The SIP gene has been found to encode at least two proteins through alternative mRNA splicing: SIP-L (L, for long; SEQ ID NO:4), and SIP-S (S, for short; SEQ ID NO:6). A sequence comparison of SIP-L to SIP-S is set forth in FIG. 1. To further identify potential targets of Siah-1-mediated ubiquitin/proteasome protein degradation, yeast two-hybrid screens of cDNA libraries were performed using the invention human SIP-L protein (SEQ ID NO:4) as a bait. Such screen resulted in the identification of Skp1 (Zhang et al., 1995, Cell, 82(6):915–925).

Figure 8:
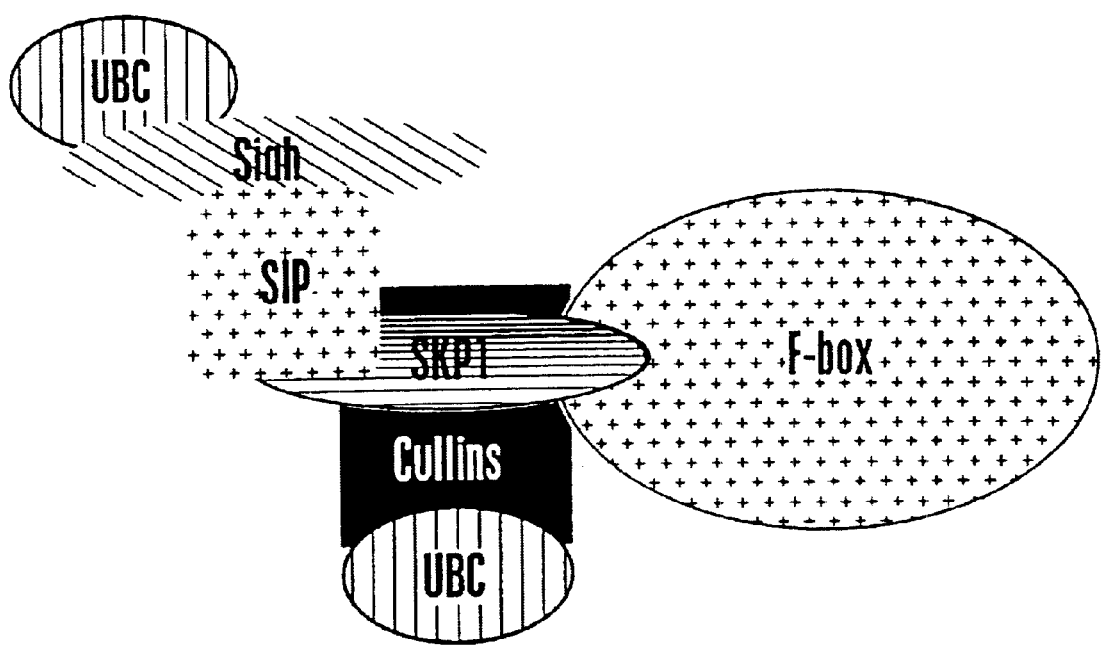
FIG. 8 shows a diagram of how an invention SIP communicates with the Protein Ubiquitination Machinery.

As shown in FIG. 8, an invention SIP protein binds simultaneously to Siah and Skp, proteins known to bind directly or indirectly, respectively, to ubiquitin-conjugating enzymes (E2s). Therefore, in accordance with the present invention, this characteristic of SIP is useful for methods for targeting desired proteins for degradation, via a ubiquitin/proteosome-dependent mechanism (see, e.g., Example 15).

In accordance with another embodiment of the invention, using a yeast two-hybrid screen with Skp1 as bait (set forth in the Examples), two additional invention SMDP and/or SCP proteins were identified as Skp1-interacting proteins, which are referred to herein as SAF-1 and SAD. As used herein the term "SAF-1" refers to Skp1-Associated F-box protein-1. The invention SAF-1 proteins, or functional fragments thereof, are characterized by having the ability to bind to at least one or more of the proteins selected from Skp1, SIP, such as SIP-L, or SAD. Invention SAF-1 proteins are further characterized as containing an "F-box" amino acid domain. Exemplary SAF-1 proteins include SAF-1α (SEQ ID NO:8) and SAF-1β (SEQ ID NO:10). An exemplary F-box domain is set forth as amino acids 256–296 of SEQ ID NO:8 and amino acids 335–375 of SEQ ID NO:10(see FIG. 6). SAF-1 beta has the same F-Box as alfa, the location is in amino acids 335–375. In accordance with the present invention, a homologue of SAF-1 protein has also been identified in the NCBI BLAST data base (Human DNA sequence from clone 341E18 on chromosome 6p11.2–12.3, AL031178) which shares significant homology with F-box domain of SAF-1. The invention homolog is referred to herein as SAF-2 and is set forth in SEQ ID Nos:11 and 12.

As used herein the term "SAD" refers to Skp1-Associated Destruction-box protein. The invention SAF-1 proteins, or functional fragments thereof, are characterized by having the ability to bind to at least one or more of the proteins selected from Skp1, SIP, such as SIP-L, or SAF-1. It is also contemplated herein that SAD has the ability to bind to SAF-2. Invention SAD proteins are further characterized as containing an "D-box" (Destruction-box) amino acid domain. An exemplary SAD protein is set forth herein as SEQ ID NO:14. As used herein, the D-box domain comprises the consensus amino acid sequence -Asp Ser Gly $Xaa_1$ $Xaa_2$ Ser-, wherein $Xaa_1$ is preferably selected from a hydrophobic amino acid, such as Tyr, Ile, Leu, Met, Phe, Trp, or Val; and $Xaa_2$ is any amino acid (see FIG. 2). A preferred D-box domain comprises the sequence set forth as amino acids 144–149 of SEQ ID NO:14.

Thus, exemplary functional fragments of an invention SAD protein comprise at least amino acids 144–149 of SEQ ID NO:14. Also contemplated herein are functional fragments of inventions SAD proteins that bind to a SIP protein, and preferably comprise at least amino acids 360–447 of SEQ ID NO:14. Functional fragments of inventions SAD proteins that bind to a Skp1 protein preferably comprise at least amino acids 128–359 of SEQ ID NO:14. Functional fragments of inventions SAD proteins that bind to a SAF-1 protein preferably comprise at least amino acids 1–127 of SEQ ID NO:14.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention SMDP and/or SCP gene or mRNA transcript in a given sample. The nucleic acid molecules described herein, and fragments thereof, are also useful as primers and/or templates in a PCR reaction for amplifying genes encoding invention proteins described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a SMDP and/or SCP. One means of isolating a nucleic acid encoding an SMDP and/or SCP polypeptide is to probe a mammalian genomic library with a natural or artificially designed DNA probe using methods well known in the art. DNA probes derived from the SMDP and/or SCP gene are particularly useful for this purpose. DNA and cDNA molecules that encode SMDP and/or SCP polypeptides can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an SMDP and/or SCP polypeptide. Such nucleic acids may include, but are not limited to, nucleic acids comprising substantially the same nucleotide sequence as set forth in SEQ ID Nos:1 (Siah-1α), 3 (SIP-L), 5 (SIP-S), 7 (SAF-1α), 9 (SAF-1β), 11 (SAF-2) and 13 (SAD).

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAS, RNAs, polypeptides or proteins as they naturally occur are not.

Invention proteins can be obtained from any species of organism, such as prokaryotes, eukaryotes, plants, fungi, vertebrates, invertebrates, and the like. A particular species can be d mammalian, As used herein, "mammalian" refers to a subset of species from which an invention SMDP and/or SCP is derived, e.g., human, rat, mouse, rabbit, monkey, baboon, bovine, porcine, ovine, canine, feline, and the like. A preferred SMDP and/or SCP herein, is human SMDP and/or SCP.

In one embodiment of the present invention, cDNAs encoding the invention SMDPs and/or SCPs disclosed herein comprise substantially the same nucleotide sequence as the coding region set forth in any of SEQ ID NOs:1, 3, 5, 7, 9, 11 and 13. Preferred cDNA molecules encoding the invention proteins comprise the same nucleotide sequence as as the coding region set forth in any of SEQ ID NOs:1, 3, 5, 7, 9, 11 and 13.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID Nos:2, 4, 6, 8, 10, 12 or 14. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

This invention also encompasses nucleic acids which differ from the nucleic acids shown in SEQ ID NOs:1,3, 5, 7, 9, 11 and 13, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding SMDP and/or SCP polypeptides that, by virtue of the degeneracy of the genetic code, do not necessarily hybridize to the invention nucleic acids under specified hybridization conditions. Preferred nucleic acids encoding the invention SMDPs and/or SCPs are comprised of nucleotides that encode substantially the same amino acid sequence as set forth in SEQ ID Nos:2, 4, 6, 8, 10, 12 or 14.

Thus, an exemplary nucleic acid encoding an invention SMDP and/or SCP may be selected from:

(a) DNA encoding the amino acid sequence set forth in SEQ ID Nos:2, 4, 6, 8, 10, 12 or 14, (b) DNA that hybridizes to the DNA of (a) under moderately stringent conditions, wherein said DNA encodes biologically active SMDP and/or SCP, or (c) DNA degenerate with respect to either (a) or (b) above, wherein said DNA encodes biologically active SMDP and/or SCP.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 42° C., followed by washing in 1×SSPE, 0.2% SDS, at 50° C. Denhart's solution and SSPE (see, e.g., Sambrook et al., *Molecular Cloning, A Laboratory Manual,* Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NOs:1, 3, 5, 7, 9, 11 and 13, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NOs:1, 3, 5, 7, 9, 11 and 13.

The invention nucleic acids can be produced by a variety of methods well-known in the art, e.g., the methods described herein, employing PCR amplification using oligonucleotide primers from various regions of SEQ ID NOs:1, 3, 5, 7, 9, 11 and 13, and the like.

In accordance with a further embodiment of the present invention, optionally labeled SMDP and/or SCP-encoding cDNAs, or fragments thereof, can be employed to probe library(ies) (e.g., cDNA, genomic, and the like) for additional nucleic acid sequences encoding novel mammalian SMDPs and/or SCPs. Construction of suitable mammalian cDNA libraries is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5×standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as SEQ ID NOs:1, 3, 5, 7, 9, 11 and 13 are obtained.

As used herein, a nucleic acid "probe" is single-stranded DNA or RNA, or analogs thereof, that has a sequence of nucleotides that includes at least 14, at least 20, at least 50, at least 100, at least 200, at least 300, at least 400, or at least 500 contiguous bases that are the same as (or the complement of) any contiguous bases set forth in any of SEQ ID NOs:1, 3, 5, 7, 9, 11 and 13. Preferred regions from which to construct probes include 5' and/or 3' coding regions of SEQ ID NOs:1, 3, 5, 7, 9, 11 and 13. In addition, the entire cDNA encoding region of an invention SMDP and/or SCP, or the entire sequence corresponding to SEQ ID NOs:1, 3, 5, 7, 9, 11 and 13, may be used as a probe. Probes may be labeled by methods well-known in the art, as described hereinafter, and used in various diagnostic kits.

It is understood that a SMDP and/or SCP-encoding nucleic acid molecule of the invention, as used herein, specifically excludes previously known nucleic acid molecules consisting of nucleotide sequences having identity with the SMDP and/or SCP-encoding nucleotide sequence (e.g., SEQ ID NO:NOs:1, 3, 5, 7, 9, 11, 13), such as Expressed Sequence Tags (ESTs), Sequence Tagged Sites (STSs) and genomic fragments, deposited in public databases such as the nr, dbest, dbsts, gss and htgs databases, which are available for searching at the ncbi.nlm.nih.gov/ blast Web site, using the program BLASTN 2.0.9 described by Altschul et al., Nucleic Acids Res. 25:3389–3402 (1997).

In particular, a SMDP and/or SCP-encoding nucleic acid molecule specifically excludes nucleic acid molecules consisting of any of the nucleotide sequences having the Genbank (gb), EMBL (emb) or DDBJ (dbj) accession numbers described below. Similarly, a SMDP and/or SCP polypeptide fragment specifically excludes the amino acid fragments encoded by the nucleotide sequences having the GenBank accession numbers described below. GenBank accession numbers specifically excluded include NCBI ID: AA054272, AA258606, AA923663, AA418482, and AI167464. The human sequence referenced as GenBank accession No. AL031178 is also specifically excluded from an invention SMDP and/or SCP-encoding nucleic acid.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493, 795.

In accordance with another embodiment of the present invention, there are provided isolated mammalian Siah-Mediated-Degradation-Proteins (SMDPs) and/or SCF-Complex-Proteins (SCPs), and fragments thereof encoded by invention nucleic acid. The phrase "SMDP and/or SCP" refers to substantially pure native SMDP and/or SCP, or recombinantly produced proteins, including naturally occurring allelic variants thereof encoded by mRNA generated by alternative splicing of a primary transcript, and further including fragments thereof which retain at least one native biological activity, such as immunogenicity, the ability to bind to another member of the SMDP and/or SCP families, or to homodimerize. In another embodiment, SMDPs and/or SCPs referred to herein, are those polypeptides specifically recognized by an antibody that also specifically recognizes a SMDP and/or SCP (preferably human) including an amino acid sequence set forth in SEQ ID NOs:2, 4, 6, 8, 10, 12 and 14. Invention isolated SMDPs and/or SCPs are substantially pure and free of cellular components and/or contaminants normally associated with a native in vivo environment.

Presently preferred SMDPs and/or SCPs of the invention include proteins that comprise substantially the same amino acid sequences as the protein sequence set forth in SEQ ID NOs:2, 4, 6, 8, 10, 12 and 14, as well as biologically active, functional fragments thereof.

Those of skill in the art will recognize that numerous residues of the above-described sequences can be substituted with other, chemically, sterically and/or electronically similar residues without substantially altering the biological activity of the resulting receptor species. In addition, larger polypeptide sequences containing substantially the same sequence as amino acids set forth in SEQ ID NOs:2, 4, 6, 8, 10, 12 and 14 therein (e.g., splice variants) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention SMDP and/or SCP(s), or polypeptide fragments thereof, refers to a polypeptide that exhibits functional characteristics similar to SMDP and/or SCP. For example, one biological activity of SMDP and/or SCP is the ability to bind, preferably in vivo, to at least one other member of the SMDP and/or SCP families of proteins, or to homodimerize, or to mediate protein degradation via an SFC complex as described herein. Such SMDP and/or SCP binding activity can be assayed, for example, using the methods described herein. Another biological activity of SMDP and/or SCP is the ability to act as an immunogen for the production of polyclonal and monoclonal antibodies that bind specifically to an invention SMDP and/or SCP. Thus, an invention nucleic acid encoding SMDP and/or SCP will encode a polypeptide specifically recognized by an antibody that also specifically recognizes the SMDP and/or SCP protein (preferably human) including the amino acid set forth in SEQ ID NOs:2, 4, 6, 8, 10, 12 and 14. Such immunologic activity may be assayed by any method known to those of skill in the art. For example, a test-polypeptide encoded by a SMDP and/or SCP cDNA can be used to produce antibodies, which are then assayed for their ability to bind to an invention SMDP and/or SCP protein including the sequence set forth in SEQ ID Nos:2, 4, 6, 8, 10, 12 or 14. If the antibody binds to the test-polypeptide and the protein including the sequence encoded by SEQ ID NOs:2, 4, 6, 8, 10, 12 or 14 with substantially the same affinity, then the polypeptide possesses the requisite immunologic biological activity.

The invention SMDPs and/or SCPs can be isolated by a variety of methods well-known in the art, e.g., recombinant expression systems described herein, precipitation, gel filtration, ion-exchange, reverse-phase and affinity chromatography, and the like. Other well-known methods are described in Deutscher et al., *Guide to Protein Purification: Methods in Enzymology Vol. 182*, (Academic Press, (1990)), which is incorporated herein by reference. Alternatively, the isolated polypeptides of the present invention can be obtained using well-known recombinant methods as described, for example, in Sambrook et al., supra., 1989).

An example of the means for preparing the invention polypeptide(s) is to express nucleic acids encoding the SMDP and/or SCP in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also encompassed by the term SMDP and/or SCP are functional fragments or polypeptide analogs thereof. The term "functional fragment" refers to a peptide fragment that is a portion of a full length SMDP and/or SCP protein, provided that the portion has a biological activity, as defined above, that is characteristic of the corresponding full length protein. For example, a functional fragment of an invention SMDP and/or SCP protein can have the protein:protein binding activity prevalent in SMDPs and/or SCPs. In addition, the characteristic of a functional fragment of invention SMDP and/or SCP proteins to elicit an immune response is useful for obtaining an anti-SMDP and/or SCP antibodies. Thus, the invention also provides functional fragments of invention SMDP and/or SCP proteins, which can be identified using the binding and routine methods, such as bioassays described herein.

The term "polypeptide analog" includes any polypeptide having an amino acid residue sequence substantially the same as a sequence specifically shown herein in which one or more residues have been conservatively substituted with a functionally similar residue and which displays the ability to functionally mimic an SMDP and/or SCP as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The amino acid length of functional fragments or polypeptide anlogs of the present invention can range from about 5 amino acids up to the full-length protein sequence of an invention SMDP and/or SCP. In certain embodiments, the amino acid lengths include, for example, at least about 10 amino acids, at least about 20, at least about 30, at least about 40, at least about 50, at least about 75, at least about 100, at least about 150, at least about 200, at least about 250 or more amino acids in length up to the full-length SMDP and/or SCP protein sequence.

As used herein the phrase "conservative substitution" also includes the use of a chemically derivatized residue in place of a non-derivatized residue, provided that such polypeptide displays the required binding activity. The phrase "chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues, relative to the sequence of a polypeptide whose sequence is shown herein, so long as the required activity is maintained.

The present invention also provides compositions containing an acceptable carrier and any of an isolated, purified SMDP and/or SCP mature protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents. The SMDP and/or SCP compositions described herein can be used, for example, in methods described hereinafter.

Also provided are antisense-nucleic acids having a sequence capable of binding specifically with full-length or any portion of an mRNA that encodes SMDP and/or SCP polypeptides so as to prevent translation of the mRNA. The antisense-nucleic acid may have a sequence capable of binding specifically with any portion of the sequence of the cDNA encoding SMDP and/or SCP polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

Compositions comprising an amount of the antisense-nucleic acid, described above, effective to reduce expression of SMDP and/or SCP polypeptides by passing through a cell membrane and binding specifically with mRNA encoding SMDP and/or SCP polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense-nucleic acid compositions are useful to inhibit translation of mRNA encoding invention polypeptides. Synthetic oligonucleotides, or other antisense chemical structures are designed to bind to mRNA encoding SMDP and/or SCP polypeptides and inhibit translation of mRNA and are useful as compositions to inhibit expression of SMDP and/or SCP associated genes in a tissue sample or in a subject.

In accordance with another embodiment of the invention, kits are provided for detecting mutations, duplications, deletions, rearrangements and aneuploidies in SMDP and/or SCP genes comprising at least one invention probe or antisense nucleotide.

The present invention provides means to modulate levels of expression of SMDP and/or SCP polypeptides by employing synthetic antisense-nucleic acid compositions (hereinafter SANC) which inhibit translation of mRNA encoding these polypeptides. Synthetic oligonucleotides, or other antisense-nucleic acid chemical structures designed to recognize and selectively bind to mRNA, are constructed to be complementary to full-length or portions of an SMDP and/or SCP coding strand, including nucleotide sequences set forth in SEQ ID NOs:1, 3, 5, 7, 9, 11 and 13. The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed supra. The SANC is also designed to recognize and selectively bind to target mRNA sequence, which may correspond to a sequence contained within the sequences shown in SEQ ID NOs:1, 3, 5, 7, 9, 11 and 13. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SANCs have been shown to be capable of such properties when directed against mRNA targets (see Cohen et al., *TIPS*, 10:435 (1989) and Weintraub, *Sci. American,* January (1990), pp. 40; both incorporated herein by reference).

In accordance with yet another embodiment of the present invention, there is provided a method for the recombinant production of invention SMDPs and/or SCPs by expressing the above-described nucleic acid sequences in suitable host cells. Recombinant DNA expression systems that are suitable to produce SMDPs and/or SCPs described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., *Meth. in Enzymology*, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system [described by Mulligan and Berg, *Nature Vol.* 277:108–114 (1979)] the Okayama-Berg cloning system [*Mol. Cell Biol.* Vol. 2:161–170 (1982)], and the expression cloning vector described by Genetics Institute [*Science* Vol. 228:810–815 (1985)], are available which provide substantial assurance of at least some expression of the protein of interest in the transformed eukaryotic cell line.

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning: A Laboratory Manual* (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris;* see, e.g., U.S. Pat. Nos. 4,882,279, 4,837,148, 4,929,555 and 4,855,231), mammalian cells (e.g., HEK293, CHO and Ltk⁻ cells), insect cells, and the like. Presently preferred host organisms are bacteria. The most preferred bacteria is *E. coli*.

In one embodiment, nucleic acids encoding the invention SMDPs and/or SCPs can be delivered into mammalian cells, either in vivo or in vitro using suitable viral vectors well-known in the art. Suitable retroviral vectors, designed specifically for "gene therapy" methods, are described, for example, in WIPO publications WO 9205266 and WO 9214829, which provide a description of methods for efficiently introducing nucleic acids into human cells. In addition, where it is desirable to limit or reduce the in vivo expression of the invention SMDP and/or SCP, the introduction of the antisense strand of the invention nucleic acid is contemplated.

Viral based systems provide the advantage of being able to introduce relatively high levels of the heterologous nucleic acid into a variety of cells. Suitable viral vectors for introducing invention nucleic. acid encoding an SMDP and/or SCP protein into mammalian cells (e.g., vascular tissue segments) are well known in the art. These viral vectors include, for example, Herpes simplex virus vectors (e.g., Geller et al., *Science*, 241:1667–1669 (1988)), Vaccinia virus vectors (e.g., Piccini et al., *Meth. in Enzymology*, 153:545–563 (1987); Cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78–84), Moloney murine leukemia virus vectors (Danos et al., *PNAS, USA*, 85:6469 (1980)), adenovirus vectors (e.g., Logan et al., *PNAS, USA*, 81:3655–3659 (1984); Jones et al., *Cell*, 17:683–689 (1979); Berkner, *Biotechniques*, 6:616–626 (1988); Cotten et al., *PNAS, USA*, 89:6094–6098 (1992); Graham et al., *Meth. Mol. Biol.*, 7:109–127 (1991)), adeno-associated virus vectors, retrovirus vectors (see, e.g., U.S. Pat. Nos. 4,405,712 and 4,650,764), and the like. Especially preferred viral vectors are the adenovirus and retroviral vectors.

For example, in one embodiment of the present invention, adenovirus-transferrin/polylysine-DNA (TfAdpl-DNA) vector complexes (Wagner et al., *PNAS, USA*, 89:6099–6103 (1992); Curiel et al., *Hum. Gene Ther.*, 3:147–154 (1992); Gao et al., *Hum. Gene Ther.*, 4:14–24 (1993)) are employed to transduce mammalian cells with heterologous SMDP and/or SCP nucleic acid. Any of the plasmid expression vectors described herein may be employed in a TfAdpl-DNA complex.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing-nucleic acids into human cells using such retroviral vectors. Other retroviral vectors include, for example, the mouse mammary tumor virus vectors (e.g., Shackleford et al., *PNAS, USA*, 85:9655–9659 (1988)), and the like.

In accordance with yet another embodiment of the present invention, there are provided anti-SMDP and/or SCP antibodies having specific reactivity with an SMDP and/or SCP polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, NY (1989) which are incorporated herein by reference).

Antibody so produced can be used, inter alia, in diagnostic methods and systems to detect the level of SMDP and/or SCP present in a mammalian, preferably human, body sample, such as tissue or vascular fluid. Such antibodies can also be used for the immunoaffinity or affinity chromatography purification of the invention SMDP and/or SCP. In addition, methods are contemplated herein for detecting the presence of an invention SMDP and/or SCP protein in a tissue or cell, comprising contacting the cell with an antibody that specifically binds to SMDP and/or SCP polypeptides, under conditions permitting binding of the antibody to the SMDP and/or SCP polypeptides, detecting the presence of the antibody bound to the SMDP and/or SCP polypeptide, and thereby detecting the presence of invention polypeptides. With respect to the detection of such polypeptides, the antibodies can be used for in vitro diagnostic or in vivo imaging methods.

Immunological procedures useful for in vitro detection of target SMDP and/or SCP polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-SMDP and/or SCP antibodies are contemplated for use herein to modulate the activity of the SMDP and/or SCP polypeptide in living animals, in humans, or in biological tissues or fluids isolated therefrom. The term "modulate" refers to a compound's ability to increase (e.g., via an agonist) or inhibit (e.g., via an antagonist) the biological activity of an invention SMDP and/or SCP protein, such as the participation in Siah-Mediated-Degradation via an SFC complex and the 26S proteosome. Accordingly, compositions comprising a carrier and an amount of an antibody having specificity for SMDP and/or SCP polypeptides effective to inhibit naturally occurring ligands or other SMDP and/or SCP-binding proteins from binding to invention SMDP and/or SCP polypeptides are contemplated herein. For example, a monoclonal antibody directed to an epitope of an invention SMDP and/or SCP polypeptide including an amino acid sequence set forth in SEQ ID NOs:2, 4, 6, 8, 10, 12 or 14, can be useful for this purpose.

The present invention further provides transgenic non-human mammals that are capable of expressing exogenous nucleic acids encoding SMDP and/or SCP polypeptides. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of SMDP and/or SCP, invention SMDPs and/or SCPs can either be overexpressed or underexpressed (such as in the well-known knock-out transgenics) in transgenic mammals.

Also provided are transgenic non-human mammals capable of expressing nucleic acids encoding SMDP and/or SCP polypeptides so mutated as to be incapable of normal activity, i.e., do not express native SMDP and/or SCP. The present invention also provides transgenic non-human mammals having a genome comprising antisense nucleic acids complementary to nucleic acids encoding SMDP and/or SCP polypeptides, placed so as to be transcribed into antisense mRNA complementary to mRNA encoding SMDP and/or SCP polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NOs:1, 3, 5, 7, 9, 11 and 13. An example of a non-human transgenic mammal is a transgenic mouse. Examples of tissue specificity-determining elements are the metallothionein promoter and the L7 promoter.

Animal model systems which elucidate the physiological and behavioral roles of SMDP and/or SCP polypeptides are also provided, and are produced by creating transgenic animals in which the expression of the SMDP and/or SCP polypeptide is altered using a variety of techniques. Examples of such techniques include the insertion of normal or mutant versions of nucleic acids encoding an SMDP and/or SCP polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of SMDP and/or SCP genes with the native gene locus in transgenic animals, to alter the regulation of expression or the structure of SMDP and/or SCP polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of SMDP and/or SCP polypeptides.

In contrast to homologous recombination, microinjection adds genes to the host genome, without removing host genes. Microinjection can produce a transgenic animal that is capable of expressing both endogenous and exogenous SMDP and/or SCP. Inducible. promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit SMDP and/or SCP protein responses.

SMDP and/or SCP proteins, such as Siah-1, are contemplated herein to be a tumor suppressor proteins. Tumor suppressor proteins generally are thought to have a function in signal transduction. Mutation results in loss of function whereupon a signal pathway that the suppressor protein regulates is left in the "on" position, which results in unregulated cell proliferation resulting in cancerous tumor formation. Nearly all tumor suppressors regulate cell division, and proliferation, and may have involvement in biochemical pathways of development and the cell cycle.

The functions of the invention SMDP and/or SCP proteins support the role of both Siah and the invention SMDPs and/or SCPs in cellular pathways that affect protein degradation, such as by activating or inhibiting protein degradation, cell division and proliferation. Accordingly, invention SMDP and/or SCP proteins provide targets for treating a broad variety of pathologies, such as proliferative diseases, cancer pathologies, and the like.

For example, in accordance with yet another embodiment of the present invention, Siah-1 has been found to bind to the protein APC (Kinzler, et al., 1996, supra). The APC protein is known to bind to β-catenin and target it for ubiquitination and degradation (Korinek, V. et al., 1997, *Science*, 275:1784–1786, Rubinfeld, B. et al., 1997, *Science*, 275:1790–1792, and Morin, P. J. et al., 1997, *Science*, 275:1787–1790). Defects in the regulation of the APC/β-catenin pathway for cell growth control have been implicated in a variety of cancer pathologies, such as epithelial cancers, and the like. Thus, in accordance with the present invention Siah-1, and antagonist or agonists thereof, are contemplated for use in methods for treating a variety of cancers, such as epithelial cancer and the like, preferably by modulating β-catenin degradation. When used for binding to APC, fragments comprising the carboxy terminus of Siah-1, preferably comprising at least amino acids 252–298 of SEQ ID NO:2, are employed (See FIG. 3).

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of invention proteins or fragments thereof.

Thus, in accordance with yet another embodiment of the present invention, there are provided methods for identifying compounds which bind to, and preferably, modulate the activity of SMDP and/or SCP polypeptides. The invention proteins may be employed in a competitive binding assay. Such an assay can accommodate the rapid screening of a large number of compounds to determine which compounds, if any, are capable of binding to SMDPs and/or SCPs. Subsequently, more detailed assays can be carried out with those compounds found to bind, to further determine whether such compounds act as modulators, agonists or antagonists of invention SMDP and/or SCP proteins. Compounds that bind to and/or modulate invention SMDPs and/or SCPs can be used to treat a variety of pathologies mediated by invention SMDPs and/or SCPs, as described herein.

In accordance with another embodiment of the present invention, transformed host cells that recombinantly express invention polypeptides can be contacted with a test compound, and the modulating effect(s) thereof can then be evaluated by comparing the SMDP-mediated response (e.g., the degradation of a known Siah-mediated target, such as DCC or β-catenin) in the presence and absence of test compound, or by comparing the response of test cells or control cells (i.e., cells that do not express SMDP and/or SCP polypeptides), to the presence of the compound.

As used herein, a compound or a signal that "modulates the activity" of invention polypeptides refers to a compound or a signal that alters the activity of SMDP and/or SCP polypeptides so that the activity of the invention polypeptide is different in the presence of the compound or signal than in the absence of the compound or signal. In particular, such compounds or signals include agonists and antagonists. An agonist encompasses a compound or a signal that activates SMDP and/or SCP protein expression. Alternatively, an antagonist includes a compound or signal that interferes with SMDP and/or SCP expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate SMDP and/or SCP activity generally require comparison to a control. For example, one type of a "control" is a cell or culture that is treated substantially the same as the test cell or test culture exposed to the compound, with the distinction that the "control" cell or culture is not exposed to the compound. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

Accordingly, in accordance with another embodiment of the present invention, there is provided a bioassay for evaluating whether test compounds are capable of acting as agonists or antagonists for SMDP and/or SCP proteins, wherein said bioassay comprises:
(a) culturing cells containing:
DNA which expresses an SMDP and/or SCP or functional fragments thereof,
wherein said culturing is carried out in the presence of at least one compound whose ability to modulate an activity of an SMDP and/or SCP is sought to be determined, wherein said activity is selected from a protein:protein binding activity or a protein degradation activity and thereafter
(b) monitoring said cells for either an increase or decrease in the level of protein:protein binding or protein degradation.

Methods well-known in the art for measuring protein:protein binding or protein degradation can be employed in bioassays described herein to identify agonists and antagonists of SMDP and/or SCP proteins. For example, the Siah-1 over-expression assay described in Example 14 can be used to evaluate the cell degradation activity of recombinant SMDP and/or SCP proteins or mutants and/or analogs thereof, expressed in mammalian host cells.

As used herein, "ability to modulate protein degradation activity of an SMDP and/or SCP" protein refers to a compound that has the ability to either induce (agonist) or inhibit (antagonist) the protein degradation activity of SMDP and/or SCP proteins within a cell. Host cells contemplated for use in the bioassay(s) of the present invention include human and other mammalian cells (readily avaialable from American Type Culture Collection), as well as genitically engineered yeast or bacteria that express human SMDPs and/or SCPs, and the like.

In yet another embodiment of the present invention, there are provided methods for modulating the protein degradation activity mediated by SMDP and/or SCP protein(s), said method comprising:

contacting an SMDP and/or SCP protein with an effective, modulating amount of an agonist or antagonist identified by the above-described bioassays.

Also provided herein are methods of treating pathologies, said method comprising administering an effective amount of an invention therapeutic composition. Such compositions are typically administered in a physiologically compatible composition.

Exemplary diseases related to abnormal cell proliferation contemplated herein for treatment according to the present invention include cancer pathologies, keratin hyperplasia, neoplasia, keloid, benign prothetic hypertrophy, inflammatory hyperplasia, and the like. Exemplary cancer pathologies contemplated herein for treatment include, gliomas, carcinomas, sarcomas, melanomas, hamartomas, leukemias, lymphomas, and the like.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

Accordingly, the present invention contemplates therapeutic compositions useful for practicing the therapeutic methods described herein. Therapeutic compositions of the present invention, such as pharmaceutical compositions, contain a physiologically compatible carrier together with an invention SMDP and/or SCP (or functional fragment thereof), a SMDP and/or SCP modulating agent, such as a compound (agonist or antagonist) identified by the methods described herein, or an anti-SMDP and/or SCP antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable of administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and -aryl amines (e.g., triethylamine, diisopropyl amine, methyl amine, dimethyl amine, and the like) and optionally substituted ethanolamines (e.g., ethanolamine, diethanolamine, and the like).

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary additional liquid phases include glycerin, vegetable oils such as cottonseed oil, and water-oil emulsions.

As described herein, an "effective amount" is a predetermined amount calculated to achieve the desired therapeutic effect, e.g., to modulate the protein degradation activity of an invention SMDP and/or SCP protein. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as discussed hereinafter. A therapeutically effective amount is typically an amount of an SMDP and/or SCP-modulating agent or compound identified herein that, when administered in a physiologically acceptable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml. Therapeutic invention anti-SMDP and/or SCP antibodies can be administered in proportionately appropriate amounts in accordance with known practices in this art.

Also provided are systems using invention SMDPs and/or SCPs, or functional fragments thereof, for targeting any desired protein for ubiquitination and degradation, thus enabling novel gene discovery through functional genomics strategies or providing the basis for ablating target proteins involved in diseases for therapeutic purposes.

In accordance with another embodiment of the invention, there are provided methods for "inducing the degradation of the function" of a desired protein from a particular cell or cell-system. As used herein the phrase "inducing the degradation of the function" refers to deleting, altering, modifying and/or degrading a target protein so that it no longer has the ability to perform its native physiological function. This method is useful to determine the physiological/cellular function of the degraded protein. Thus, this invention method is useful in alleviating one of the rate limiting steps in functional genomics.

The invention methods take advantage of the invention SMDP and/or SCP proteins provided herein to create a system that targets specific proteins for degradation by recruiting them to a SCF complex for ubiquitination and subsequent degradation by an appropriate proteosome, such as 26S proteosome. First, a protein or peptide fragment is selected that binds the protein targeted for degradation in a cell, which is referred to herein as the "target-protein binding domain." Such protein or peptide fragment could be, for example: a domain of any known protein that interacts with the target protein; the Fab region of an anti-target-protein antibody (e.g., sFv, and the like); or a peptide aptamer obtained by screening (using, for example, yeast two-hybridization, phage display, or other screening methods) a random library of peptide aptamers. The target-protein binding domain is then fused (by engineering cDNAs in expression plasmids to form a chimera) with an appropriate protein-degradation binding domain selected from an invention SMDP and/or SCP, such as Siah, SIP, SAF-1, SAF-2 or SAD, and the like; or other known proteins involved in protein degradation, such as F-box containing proteins, (e.g., Skp1, and the like), SOCS-box containing proteins (see, e.g., Kamura et al., 1998, *Genes Dev*, 12:3872; and Starr and Hilton, 1999, *Bioessays,*21:47), HECT family proteins (see, e.g., Huibregtse et al. 1995 *Proc. Natl. Acad. Sci. USA* 92:2563–2567), or any other subunit of an E3 ubiquitin ligase complex, and the like (see, e.g., Tyers and Williams, 1999, *Science*, 284:601–604; incorporated herein by reference in its entirety).

As used herein, the phrase "protein-degradation binding domain" refers to a protein region that functions to recruit the target protein into a member of the superfamily of E3 ubiquitin ligase complexes, such as the SCF complex, or to Siah-family proteins which may target some proteins for degradation independently of SCF complexes, where the protein-degradation binding domain and/or the target protein become ubiquitinated and then degraded, such as by the 26S proteosome, lysosomes and/or vacuoles (see, e.g., Tyers and Williams, 1999, *Science*, 284:601–604; and Ciechanover, 1998, supra). Exemplary protein-degradation domains can be obtained from a protein member of the ubiquitin-mediated protein-degradation family. As used herein, the phrase "a protein member of the ubiquitin-mediated protein-degradation family" refers to one of the numerous proteins that are known to interact, via protein-:protein binding, in the ubiquitin system of intracellular protein degradation (see, e.g., Ciechanover et al., 1998, supra; and Tyers and Williams, supra, and the like).

In yet another embodiment contemplated by the present invention, methods are provided of identifying a nucleic acid molecules encoding a chimeric protein that modulates a cellular phenotype, said method comprising:
 (a) expressing, in a cell, a chimeric nucleic acid comprising a member of a nucleic acid library fused to nucleic acid encoding a protein degradation binding domain of a protein member of the ubiquitin-mediated protein degradation family; and
 (b) screening said cells for a modulation of said phenotype.

For example, unbiased nucleic acid libraries can be constructed wherein, each member of the nucleic acid library is expressed as an encoded protein fused to a particular protein-degradation binding domain, such as invention SMDPs and/or SCPs, e.g., Siah-1, SIP (see, e.g., Example 15), SAF-1, SAF-2, or SAD; or other known proteins involved in protein degradation, such as Skp1, F-box containing proteins, HECT family proteins, or any other subunit of an E3 ubiquitin ligase complex, and the like. As used herein a "nucleic acid library" comprises cDNA libraries, YAC libraries, BAC libraries, cosmid libraries, or any other source of nucleic acid encoding polypeptides. The chimeric nucleic acid encoding these fusion proteins is then introduced into cells possessing a particular phenotype to be assayed.

The cells are then subjected to a "screening" step which comprises selecting one or more cells in which the desired phenotype has been modulated (e.g., suppressed or enhanced). The phenotypes to be screened may be any chemical or physical representation of a cellular process, including but not limited to: cell proliferation in either an attached or detached (i.e., anchorage-independent) state, cell survival, cell death, cell secretion, cell migration, abnormal cell morphology, chemical reactivity (e.g., heavy metals, antibiotics, etc.), physical reactivity (e.g., heat, light, radiation, etc.), and the like.

Next, cDNAs are identified and isolated whose expression products function to modulate the desired phenotype within cells. The cDNAs identified by the invention method encode an invention chimeric protein that interacts, preferably by direct binding, with another protein in the cells that is targeted for degradation, thereby eliminating its physiological function. Accordingly, any target-protein that has one or more protein-binding or protein-interacting partners, or which homodimerizes/homo-oligomerizes is contemplated for degradation in the invention methods. The cDNA identified by the above-described method can be used to perform a two-hybrid screen, as described herein, to identify the protein-binding region of the partner to the target protein, or directly sequenced to determine the identity of the target protein if homo-dimerization or homo-oligomerization situation occurs.

Accordingly, also provided in accordance with the present invention are chimeric proteins, and encoding nucleic acids, comprising a target-protein binding domain operatively linked to a protein-degradation binding domain of a protein member of the ubiquitin-mediated protein-degradation family.

Exemplary proteins whose function can be targeted for degradation according to the invention methods, include any protein encoded by a known gene or cDNA whose function is desired. Exemplary targets include, for example, apoptosis-related proteins, cell-cycle regulatory proteins, heat shock proteins, transcription factors, or any other target protein which, when degraded, will modulate the phenotype of a cell.

Also provided are methods for treating a disease by degrading the function of a target protein, comprising introducing, into a cell, a chimeric protein comprising a target-protein binding domain operatively linked to a protein-degradation binding domain of a protein member of the ubiquitin-mediated protein-degradation family. For example, for a variety of proteins which, when expressed in overabundant or mutated form (e.g., an oncoprotein such as ras, or a genetic mutation, such as in the CF gene (cystic fibrosisgene) result in a known pathology, the chimeric protein of the invention may be used to therapeutically treat the disease, by way of reducing or completely eliminating, via protein degradation, the pathology causing protein. This treatment comprises fusion of a protein domain which binds the target pathology causing protein (i.e., the protein which causes the illness) with a particular protein-degradation binding domain as described herein. This chimeric protein may then be delivered to the location of the protein which causes the illness by intravenous therapy or gene therapy employing the methods described herein, or any other method well-known to one skilled in the art for delivering a protein to its binding target. As used herein, "treatment of a disease" refers to a reduction in the effects of the disease, including reducing the symptoms of the disease.

In accordance with another embodiment of the present invention, there are provided methods for diagnosing cancer, said method comprising:

detecting, in said subject, a defective sequence or mutant of SEQ ID NOs:1, 3, 5, 7, 9, 11 and 13.

In accordance with another embodiment of the present invention, there are provided diagnostic systems, preferably in kit form, comprising at least one invention nucleic acid in a suitable packaging material. The diagnostic nucleic acids are derived from the SMDP and/or SCP-encoding nucleic acids described herein. In one embodiment, for example, the diagnostic nucleic acids are derived from any of SEQ ID NOs:1, 3, 5, 7, 9, 11 and 13. Invention diagnostic systems are useful for assaying for the presence or absence of nucleic acid encoding SMDP and/or SCP in either genomic DNA or in transcribed nucleic acid (such as mRNA or cDNA) encoding SMDP and/or SCP.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding SMDP and/or SCP including the nucleotide sequences set forth in SEQ ID NOs:1, 3, 5, 7, 9, 11 and 13 or mutations or deletions therein, thereby diagnosing the presence of, or a predisposition for, cancer. In addition, the packaging material contains instructions indicating how the materials within the kit are employed both to detect a particular sequence and diagnose the presence of, or a predisposition for, cancer.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

EXAMPLES

Unless otherwise stated, the present invention was performed using standard procedures, as described, for example in Maniatis et al., *Molecular Cloning: A Laboratory Manual,* Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y. USA (1989); Davis et al., *Basic Methods in Molecular Biology,* Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987)).

Two-hybrid Assays

Library screening by the yeast two-hybrid method was performed herein as described (Durfee et al., 1993; Sato et al., 1995; Matsuzawa et al. 1998) using the pGilda plasmid encoding the desired amino acid region as bait, an appropriate cDNA library, and the EGY48 strain *S.cerevisiae* (MATa, trp1, ura3, his, leu2::plexApo6-leu2). Cells were grown in either YPD medium with 1% yeast extract, 2% polypeptone, and 2% glucose, or in Burkholder's minimal medium (BMM) fortified with appropriate amino-acids as described previously (Sato et al., 1994). Transformations were performed by a LiCl method using 0.25 mg of pJG4-5-cDNA library DNA, and 5 mg of denatured salmon sperm carrier DNA. Clones that formed on Leu deficient BMM plates containing 2% galactose/1% raffinose were transferred to BMM plates containing leucine and 2% glucose, and filter assays were performed for β-galactosidase measurements as previously described.

1. Yeast Two-hybrid Screen of BAG-1 Binding Proteins to Obtain cDNA Encoding Siah-1α

The mouse BAG-1 amino acid sequence was cloned into the pGilda plasmid and used as bait to screen a human Jurkat T-cell cDNA library. From an initial screen of ~1.6×10$^7$ transformants, 298 clones were identified that transactivated the LEU2 reporter gene based on ability to grow on leucine-deficient media. Of those, 30 colonies were also positive for β-galactosidase. These 30 candidate transformants were then cured of the LexA/BAG-1 bait plasmid by growth in media containing histidine and then mated with each of 5 different indicator strains of cells containing one of following LexA bait proteins: BAG-1 (1–219), Bax (1–171), v-Ras, Fas (191–335), or Lamin-C. The mating strain was RFY206 (MATa, his3D200, leu2-3, lys2D201, ura3-52, trp1D::hisG), which had been transformed with pGilda-BAG-1 or various control proteins and selected on histidine-deficient media. This resulted in 23 clones which displayed specific two-hybrid binding interactions with BAG-1. DNA sequencing analysis revealed 4 cDNAs encoding portions of Siah-1.

2. Isolation of Full-length Human Siah-1α cDNAs

To obtain the complete sequence of human Siah-1, cDNA fragments containing the 5' end of human Siah 1 were PCR-amplified from Jurkat randomly primer cDNAs by using a forward primer 5' GGGAATTCGGACTTATGGCATGTAAACA-3' (SEQ ID NO:42) containing an EcoRI site and a reverse primer 5' TAGCCAAGTTGCGAATGGA-3' (SEQ ID NO:43), based on sequences of EST database clones (NCBI ID: AA054272, AA258606, AA923663, AA418482, and AI167464). The PCR products were digested with EcoRI and BamHI, then directly subcloned into the EcoRI and SalI sites of pcI plasmid into which the cDNA derived from pJG4-5-Siah (22–298) had previously been cloned, as a BamHI—XhoI fragment. The complete human Siah-1α cDNA and amino acid sequence is set forth in SEQ ID Nos:1 and 2, respectively. The human Siah-1α sequence contains 16 N-terminal amino acids that are not present in the human Siah-1β protein.

3. Yeast Two-hybrid Screen of Siah-1 Binding Proteins to Obtain cDNA Encoding SIP-L and SIP-S Human Siah-1α cDNA encoding amino acids 22–298 of SEQ ID NO:1 (corresponding to amino acids 6–282 set forth in Nemani et al., supra) was cloned into the pGilda plasmid and used as a bait to screen a human embryonic brain cDNA library (Invitrogen) in EGY48 strain S.cerevisiae. From an initial screen of ~2.0×10$^7$ transformants, 322 clones were identified that trans-activated the LEU2 reporter gene based on ability to grow on leucine-deficient media. Of those, 32 colonies were also positive for β-galactosidase. These 32 candidate transformants were then cured of the LexA/Siah-1 bait plasmid by growth in media containing histidine and then mated with each of 5 different indicator strains of cells containing one of following LexA bait proteins: Siah-1 (22–298), Bax (1–171), v-Ras, Fas (191–335), or BAG-1. The mating strain was RFY206 which had been transformed with pGilda-Siah-1 or various control proteins and selected on histidine-deficient media. This resulted in 11 clones which displayed specific two-hybrid interactions with Siah-1. DNA sequencing analysis revealed 5 cDNAs encoding portions of SIP-L, 1 cDNA encoding portions of SIP-S, 3 cDNAs encoding portions of of APC(2681–2843), and 2 cDNAs encoding portions of Siah-1. The SIP-L and SIP-S clones were sequenced and the resulting nucleotide sequences are set forth in SEQ ID Nos:3 and 5, respectively.

4. Yeast Two-hybrid Screen of Skp1 Binding Proteins to Obtain cDNA Encoding SAF-1 and SAD Human Skp1 cDNA encoding amino acids 91–163 of (Zhang et al., 1995, *Cell*, 82:915–925) was cloned into the pGilda plasmid as a bait to screen a human embryonic brain cDNA library (Invtrogen) in EGY48 strain S.cerevisiae. From an initial screen of ~1.2×10$^8$ transformants, 130 clones were identified that trans-activated the LEU2 reporter gene based on ability to grow on leucine-deficient media. Of those, 36 colonies were also positive for β-galactosidase. These 36 candidate transformants were then cured of the LexA/BAG-1 bait plasmid by growth in media containing histidine and then mated with each of 5 different indicator strains of cells containing one of following LexA bait proteins: Skp1 (91–163), SIP-L, Bax (1–171), v-Ras, Fas (191–335), or Siah-1. The mating strain was RFY206 which had been transformed with pGilda-Skp1 or various control proteins and selected on histidine-deficient media. This resulted in 3 clones which displayed specific two-hybrid interactions with Skp1 and 18 clones clones which displayed specific two-hybrid interactions with both Skp1 and SIP-L. DNA sequencing analysis revealed. 12 cDNAs encoding portions of SAF-1 and 9 cDNAs encoding portions of SAD. The SAF-1 and SAD clones were sequenced and the resulting nucleotide sequences are set forth in SEQ ID Nos:7 (SAF-1α), 9 (SAF-1β), and 13 (SAD).

5. Isolation of Full-length SAF-2 cDNAs

Full-length cDNA encoding a human SAF-2 protein was PCR-amplified from ZAPII Jurkat cDNA labrary (Stratagene) by using a forward primer 5'-GTGAATTCATGCAACTTGTACCTGATATAGAG TTC-3' (SEQ ID NO:44) containing an EcoRI site and a reverse primer 5'-GGACTCGAGGCTCTACAGAGGCC-3' (SEQ ID NO:45), based on human DNA sequence from clone 341E18 on chromosome 6p11.2–12.3 (AL031178). The PCR products were digested with EcoRI and XhoI, then directly subcloned into the EcoRI and XhoI sites of the plasmid pcDNA3. The corresponding plasmid was sequenced and the results are set forth in SEQ ID Nos: 11 and 12.

6. Yeast Two-hybrid Screen of SIP-L Binding Proteins

The human SIP-L cDNA encoding full-length SIP-L was cloned into the pGilda plasmid as a bait to screen a human embryonic brain cDNA library (Invtrogen) in EGY48 strain S.cerevisiae. From an initial screen of ~1.5×10$^7$ transformants, 410 clones were identified that trans-activated the LEU2 reporter gene based on ability to grow on leucine-deficient media. Of those, 68 colonies were also positive for β-galactosidase. These 32 candidate transformants were then cured of the LexA/SIP-L bait plasmid by growth in media containing histidine and then mated with each of 32 different indicator strains of cells containing one of following LexA bait proteins: SIP-L, Bax (1–171), v-Ras, Fas (191–335), or BAG-1. The mating strain was RFY206 which had been transformed with pGilda-SIP-L or various control proteins and selected on histidine-deficient media. This resulted in 16 clones which displayed specific two-hybrid interactions with SIP-L. DNA sequencing analysis revealed 3 cDNAs encoding portions of Skp1, 1 cDNA encoding portions of Siah-1, and 11 cDNAs encoding portions of SIP-L. These results indicate that SIP-L binds to Skp1 and Siah-1 proteins, and is able to homodimerize with SIP isoforms.

7. A Cell Proliferation Functional Assay of SIP/Siah Interaction

Figure 4:
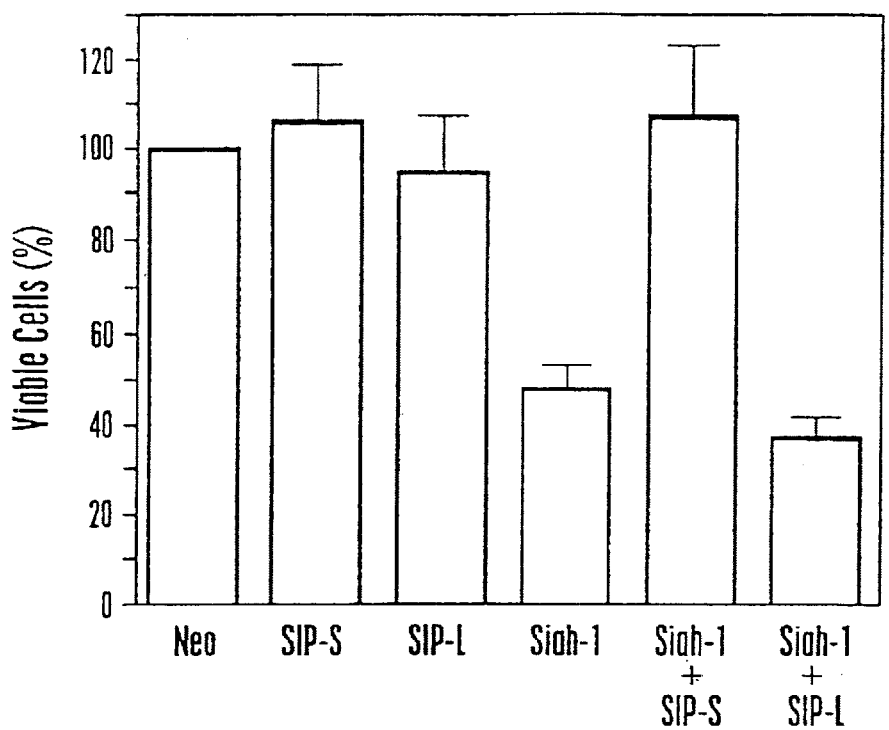
FIG. 4 shows the results of the cell proliferation functional assay of SIP/Siah interaction described in Example 7.

The effects of invention SIP-L and SIP-S proteins on Siah-1-induced cell cycle arrest in 293T epithelial cancer cells was examined and the results are shown in FIG. 4. Human embryonic kidney 293 cells were maintained in high-glucose DMEM medium containing 10% fetal calf serum, 1 mM L-glutamine, and antibiotics. Cells (~5×10$^5$) in 60 mm plates were transfected with a total of 3.0 µg of plasmid DNAs encoding Siah-1 alone or together with SIP or SIP-S by a calcium phosphate precipitation technique. After 24 hours, the cells were harvested and the number of viable and dead cells were counted using trypan blue dye exclusion assays. Efficiency of transient transfection was estimated by in situ β-galactosidase assay using a portion of the transfected cells. The transient transfection efficiency of the T293 cells was consistently 90%.

As revealed in FIG. 4, over-expression of Siah-1 resulted in decreased numbers of viable cells after 24 hours, without an increase in cell death. Thus, Siah-1 suppresses proliferation of 293 cells. Co-transfection of SIP-L with Siah-1 did not substantially alter Siah-1-mediated growth suppression. In contrast, the SIP-S protein abrogated the growth suppressive effects of Siah-1, which indicates that the invention SIP-S protein affects Siah-1 intracellularly in a different manner than SIP-L.

8. In vitro SIP:Siah-1 Protein Interaction Assays

Complementary cDNA encoding SIP-L was cloned into pGEX-4T-1 and expressed in XL-1-blue cells (Stratagene, Inc.), and affinity-purified using glutathione-Sepharose as is well-known in the art. Purified GST-fusion proteins (0.5–1.0 µg immobilized on 10–20 µl of glutathione beads) and 2.5 ul of rat reticulocyte lysates (TNT-Lysates; Promega, Inc.) containing 35S-labeled in vitro translated (IVT) Siah-1 proteins were incubated in 0.1 ml of HKMEN (10 mM HEPES [pH7.2], 142 mM KCl, 5 mM MgCl2, 2 mM EGTA, 0.1% NP-40) at 4° C. for 30 minutes. The beads were washed 3× with 1 ml HKMEN solution, followed by boiling in 25 µl of Laemmli-SDS sample buffer. The eluted proteins were analyzed by SDS-PAGE (12%) and detected by fluorography. Use of equivalent amounts of intact GST-fusion proteins and successful IVT of each protein was confirmed by SDS-PAGE analysis using Coomassie staining or autoradiography, respectively.

Figure 5A:
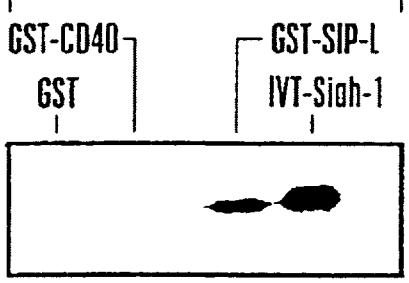
FIGS. 5A and 5B show in vitro and in vivo interaction assays of between Siah-1 and SIP-L as described in Examples 8 and 9, respectively.

The results are shown in FIG. 5A and indicate that Siah-1 binds to SIP-L and homodimerizes in vitro.

9. Co-immunoprecipitation Assay of SIP:Siah-1

Two×$10^6$ 293T cells in 100 mm plates were transiently transfected with 10 µg of pCDNA3-myc-SIP-L and 10 mg of pcDNA3-HA-Siah-1 (amino acids 97–298 of SEQ ID NO:2). Twenty-four hours later, cells were disrupted by sonication in 1 ml of HKMEN solution containing 0.2% NP-40, 0.1 µM PMSF, 5 µg/ml leupeptin, 1 µg/ml aprotinin, and 1 µg/ml pepstatin. After preclearing with normal mouse IgG and 10 ml protein A-agarose, immunoprecipitations were performed using 10 ml of anti-myc antibody-conjugated sepharose (Santa Cruz) to precipitate the myc-SIP-L fusion, or an anti-IgG as a control at 4° C. for 4 hours. After extensive washing in HKMEN solution, immune-complexes were analyzed by SDS-PAGE/immunoblotting using anti-HA antibody 12CA5 (Boehringer Mannheim), followed by HRPase-conjugated goat anti mouse immunoglobulin (Amersham, Inc.), and detected using an enhanced chemiluminescence (ECL) system (Amersham, Inc.).

Figure 5B:
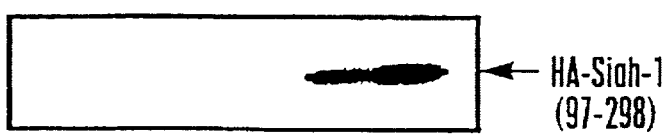

The results are shown in FIG. 5B and indicate that SIP proteins bind to Siah-1 intracellularly.

10. Yeast Two-hybrid Assay of Siah-1:APC Binding Specificity

One µg of plasmids encoding fusion proteins of the LexA DNA-binding domain fused to Siah-1, APC(2681–284), BAG-1, Bax, Ras, Fas, FLICE were co-tansformed into yeast strain EGY48 with 1 µg of pJG4-5 plasmid encoding fusion proteins of the B42 trans-activation domain fused to APC(2681–2843) and Siah-1. Transformed cells were grown on semi-solid media lacking leucine or containing leucine as a control which resulted in equivalent amounts of growth for all transformants. Plasmid combinations that resulted in growth on leucine-deficient media within 4 days were scored as positive (+). β-galactosidase activity of each colony was tested by filter assay and scored as blue (+) versus white (−) after 60 minutes.

The results are shown in Table 1, and indicate that APC interacts specifically by direct binding with Siah-1, and not with BAG-1, Bax, Ras, Fas nor FLICE.

TABLE 1

Specific Interaction of Siah with SIP

| Lex A | B42 | Leu+ | β-Gal+ |
|---|---|---|---|
| Siah-1 | APC (2681–2843) | + | + |
| APC (2681–2843) | Siah-1 | + | + |
| BAG-1 | APC (2681–2843) | − | − |

TABLE 1-continued

Specific Interaction of Siah with SIP

| Lex A | B42 | Leu+ | β-Gal+ |
|---|---|---|---|
| Bax | APC (2681–2843) | − | − |
| Ras | APC (2681–2843) | − | − |
| Fas | APC (2681–2843) | − | − |
| FLICE | APC (2681–2843) | − | − |
| empty | APC (2681–2843) | − | − |

11. Yeast Two-hybrid Assay of Siah-1:SIP Binding Specificity

One µg of plasmids encoding fusion proteins of the LexA DNA-binding domain fused to Siah-1, Siah-2, BAG-1, Bax, Ras, Fas, FLICE, and SIP-L were co-tansformed into yeast strain EGY48 with 1 µg of pJG4-5 plasmid encoding fusion proteins of the B42 trans-activation domain fused to SIP-L, SIP-S, Siah-1, Siah-2, BAG-1, Bax, and Ras. Transformed cells were grown on semi-solid media lacking leucine or containing leucine as a control which resulted in equivalent amounts of growth for all transformants. Plasmid combinations that resulted in growth on leucine-deficient media within 4 days were scored as positive (+). β-galactosidase activity of each colony was tested by filter assay and scored as blue (+) versus white (−) after 60 minutes.

The results are shown in Table 2, and indicate that SIP proteins interact specifically by direct binding with Siah proteins. SIP-L was found to interact with Siah-1 and Siah-2, and not with BAG-1, Bax, Ras, Fas nor FLICE. SIP-S was also found to interact with Siah-1. Table G also reveals that the SIP-L homodimerization domain is within amino acids 73–228 of SIP-L (SEQ ID NO:4)

Specific Interaction of Siah with SIP

TABLE 2

| Lex A | B42 | Leu+ | β-Gal+ |
|---|---|---|---|
| Siah-1 | SIP-L | + | + |
| Siah-1 | SIP-S | + | + |
| Siah-2 | SIP-L | + | + |
| BAG-1 | SIP-L | − | − |
| Bax | SIP-L | − | − |
| Ras | SIP-L | − | − |
| FLICE | SIP-L | − | − |
| empty | SIP-L | − | − |
| SIP-L | Siah-1 | + | + |
| SIP-L | Siah-2 | + | + |
| SIP-L | BAG-1 | − | − |
| SIP-L | Bax | − | − |
| SIP-L | Ras | − | − |
| SIP-L | SIP-L | + | + |
| SIP-L | SIP-S | − | − |

12. Mapping of Siah-APC Interaction Domains

Expression plasmids encoding fusion proteins of Siah-1α fragments corresponding to: SEQ ID NO:2 amino acids 22–298; 22–251; 22–193; 97–298; and 46–102, fused to the B-42 trans-activation domain were co-transformed into yeast EGY48 cells with a plasmid encoding a chimeric fusion protein of the Lex A DNA-binding domain fused to amino acids 2681–2843 of APC "APC(2681–2843)." Transformed cells were grown on semi-solid media lacking leucine or containing leucine as a control. Plasmid combinations that resulted in growth on leucine-deficient media within 4 days were scored as positive (+). β-galactosidase activity for each colony was tested by filter assay and scored as blue (+) versus white (−) (β-gal) based on a 1 hour of color development.

The results are shown in FIG. 3 and indicate that a region within the 47 carboxy terminal amino acids of Siah-1α (SEQ ID NO:2) is required for binding to APC.

13. Mapping of SKP-1, SIP-L, SAF-1, and SAD Interaction Domains

Expression plasmids encoding fusion proteins of SAF-1α and functional fragments thereof corresponding to SEQ ID NO:8 amino acids 68–443; 80–443; and 258–443, were fused to the B-42 trans-activation domain. Likewise, expression plasmids encoding fusion proteins of SAD and functional fragments thereof corresponding to SEQ ID NO:14 amino acids 128–447; and 360–447, were fused to the B-42 trans-activation domain. These SAF-1-fragment- and SAD-fragment-B-42 fusion proteins were co-transformed into yeast EGY48 cells with a plasmid encoding a chimeric fusion protein of the Lex A DNA-binding domain fused to either SKP1, SIP-L, SAF-1, or SAD. Transformed cells were grown on semi-solid media lacking leucine or containing leucine as a control. Plasmid combinations that resulted in growth on leucine-deficient media within 4 days were scored as positive (+). β-galactosidase activity for each colony was tested by filter assay and scored as blue (+) versus white (−) (β-gal) based on a 1 hour of color development.

Figure 6A:
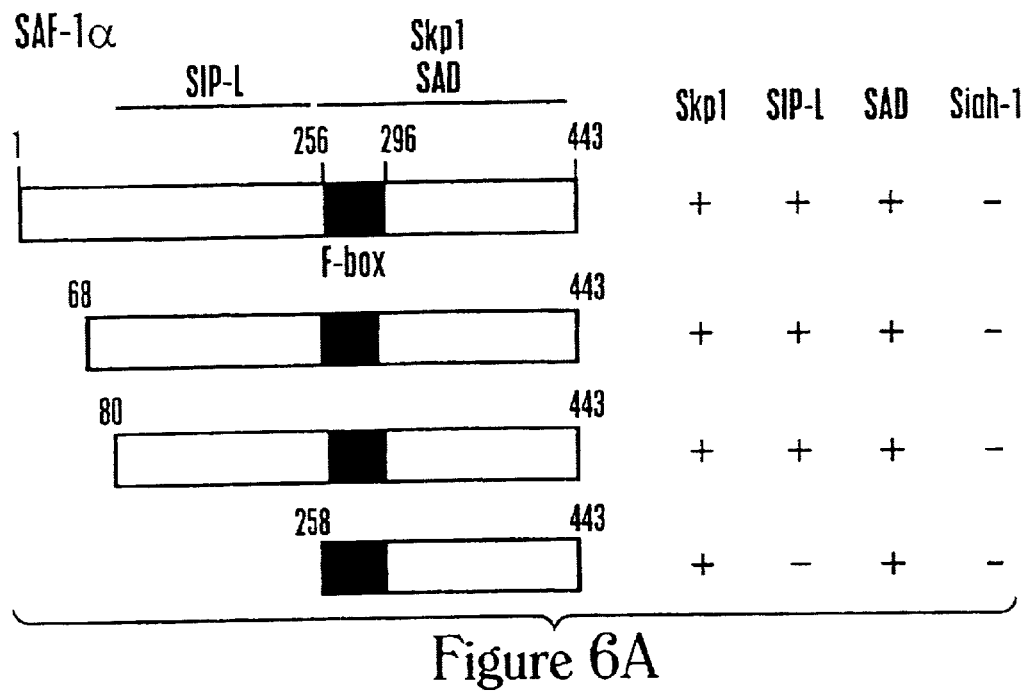
FIGS. 6A and 6B show the mapping of SKP1, SIP-L, SAF-1 and SAD interaction domains as described in Example 13.
Figure 6B:
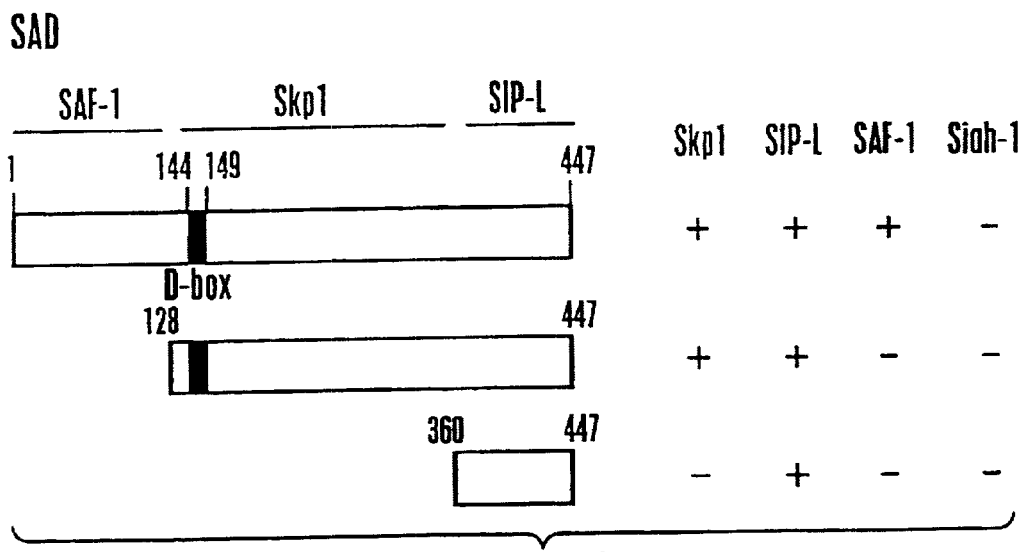

The results are shown in FIGS. 6A and 6B. FIG. 6A indicates that SAF-1 interacts by direct binding to Skp1, SIP-L and SAD, but does not interact with Siah-1. A region within the SAF-1 fragment corresponding to amino acids 80–257 of SEQ ID NO:8 is required for SIP-L interaction, whereas a region within amino acids 258–443 of SAF-1 is required for Skp1 and SAD interaction.

FIG. 6B indicates that SAD interacts by direct binding to Skp1, SIP-L and SAF-1, but does not interact with Siah-1. A region within the SAD fragment corresponding to amino acids 1–127 of SEQ ID NO:14 is required for SAF-1 interaction; a region within amino acids 128–359 of SAD is required for Skp1 interaction; and a region within amino acids 360–447 of SEQ ID NO:14 is required for SIP-L interaction.

14. Effect of Siah-1 Over-expression on Stability of β-catenin 293T cells were transiently transfected with a plasmid encoding myc-tagged β-catenin and either pcDNA3, pcDNA3-Siah-1, or pcDNA3-Siah-1(97–298; amino acids 97–298 of SEQ ID NO:2). Whole cell lysates were prepared, normalized for total protein content (25 μg per lane) and analyzed by SDS-PAGE/immunoblotting using an anti-Myc tag antibody.

Figure 7:
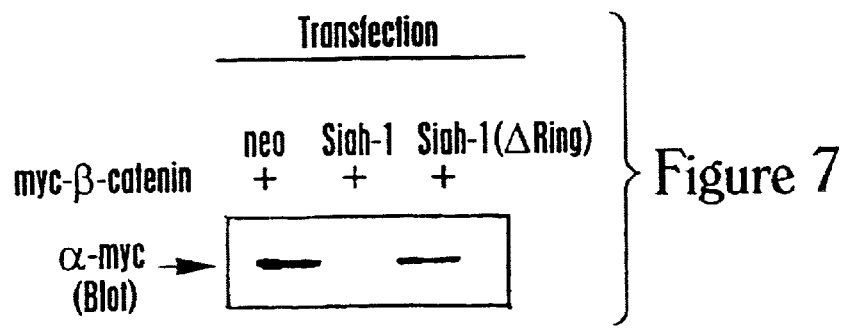
FIG. 7 shows the effect of Siah-1 overexpression on stability of β-catenin.

FIG. 7 indicates that expression of full-length Siah-1 abolishes, by degradation, the presence of β-catenin within cells, whereas expression of amino acids 97–298 of Siah-1 (SEQ ID NO:2) does not result in β-catenin degradation. Thus, a region within amino acids 1–96 of SEQ ID NO:2 (Siah-1α), which contains the N-terminal "Ring" domain, is required for protein degradation.

15. Demonstration of SIP-mediated Degradation of a Target Protein, TRAF6

Figure 9:
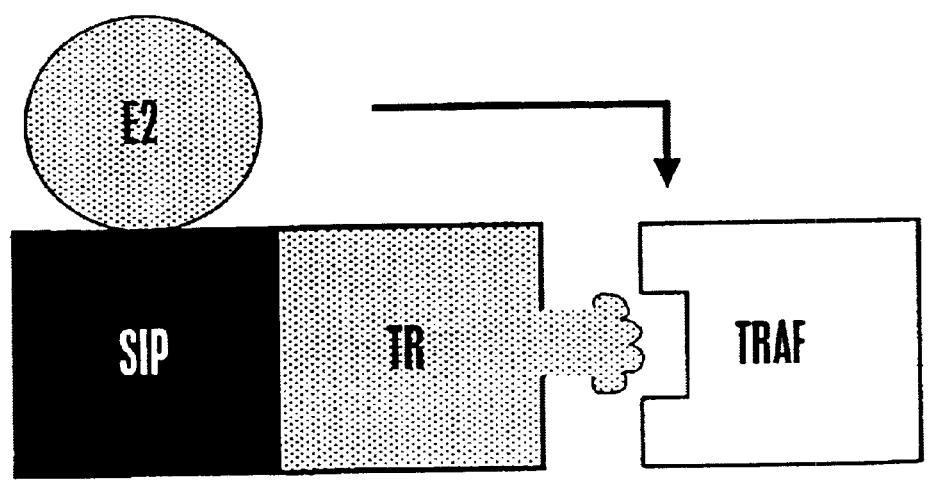
FIG. 9 shows a general diagram of an invention method for inducing targeted degradation of proteins using SIP, exemplified in Example 15.

An invention SIP-based method for targeted degradation of proteins was applied to the degradation TRAF proteins. The schematic in FIG. 9 shows the strategy employed for targeted degradation of specific TRAF-family proteins. A chimeric protein is expressed from the plasmid pcDNA3 in which SIP-L (SEQ ID NO:3) is fused with bacterial thioredoxin containing various TRAF-binding peptides displayed on the surface of thioredoxin, as described by Brent and colleagues (Colas, et al. Nature, 380: 548, 1996; Cohen, et al. Proc. Natl. Acad. Sci., 95: 14272, 1998; Geyer, et al. Proc. Natl. Acad. Sci., 96: 8562, 1999; Fabbrizio, et al. Oncogene, 18: 4357, 1999). The TRAF-binding peptide binds to a member of the TRAF-family, and targets the TRAF-protein for ubiquitination and subsequent proteosome-dependent degradation because the SIP-region of the chimeric protein recruits ubiquitin-conjugating enzymes (E2s) to the protein complex.

Isolation of Target-protein Binding Domain Peptides that Selectively Bind TRAF2 and TRAF6

A peptide aptamer library was screened by the yeast two-hybrid method to identify peptides that bind to either TRAF2 or TRAF6 using the methods described in Leo, et al. J Biol Chem, 274:22414, 1999. TRAFs are a family of signal transducing proteins involved in cytokine receptor signaling inside cells. The sequences of the resulting TRAF-binding peptides are set forth in (Tables 3 and 4).

TABLE 3

Selected Traf 2 Aptamer Clones

| Clones | (SEQ ID NO:) | SLxCIxLR motif |
|---|---|---|
| 219 | (15) | SESPGALRSG<u>SLRCISLR</u>IC |
| 230 | (16) | VCRGRIRSG<u>SLRCISLR</u>ICR |
| 221 | (17) | LLR<u>LGCIRL</u>LMLRRGVVFRL |
| 208 | (18) | VLFL<u>SLR</u>FWGLNIVVMGRLL |
| 215 | (19) | CR<u>SLGVI</u>VGGTEAAGAPTFI |
|  |  | LSmotif |
| 208 | (20) | VLF<u>LS</u>LRFWGLNIVVMGRLL |
| 213 | (21) | WLRRGLVGVFF<u>LS</u>RVMVGI |
| 218 | (22) | SLG<u>LS</u>VCIGRRAGGGFRGFG |
| 237 | (23) | RFA<u>LS</u>IGVCVVVRVGICLGM |
|  |  | LVmotif |
| 209 | (24) | SAV<u>LVL</u>VYVSAALRGRGFGI |
| 227 | (25) | HGGGRGA<u>LV</u>SVMYLCGFIRL |
|  |  | Non-Consensusmotif |
| 231 | (26) | RGRVIGMWVGLRCRMFLV |

TABLE 4

Selected Traf 6 Aptamer Clones

| Clones | (SEQ ID NO:) | WR motif |
|---|---|---|
| 625 | (27) | VDWAVYSVV<u>WR</u>YTTT* |
| 631 | (28) | KTSVILV<u>WR</u>LSFFCLYRSL* |
| 606 | (29) | ANRC<u>WR</u>E* |
| 628 | (30) | EGTLSKRM<u>WR</u>THN* |
| 640 | (31) | S<u>WR</u>DMTQSGM* |
| 604 | (32) | DVP<u>WQR</u>ACARQ * |
| 607 | (33) | LERVAR<u>WV</u>L* |
| 602 | (34) | VADVLVF<u>WG</u>YVF* |
|  |  | DVxVFmotif |
| 602 | (34) | VA<u>DVLVF</u>WGYVF* |
| 613 | (35) | G<u>DVGVF</u>PE* |
|  |  | Non-Consensusmotif |
| 603 | (36) | PEMMLEGPKYCLxLxE* |
| 609 | (37) | LLYGALA* |
| 612 | (38) | GAIKFAHESCE* |

TABLE 4-continued

Selected Traf 6 Aptamer Clones

| Clones | (SEQ ID NO:) | WR motif |
|---|---|---|
| 616 | (39) | PMAMD* |
| 632 | (40) | QEEEM* |
| 639 | (41) | ISVVHGIGSDSD* |

*Termination codon

SIP-fusion Chimeric Protein Construction

An invention SIP-fusion chimeric construct is generated by combining the open reading frame (ORF) of $SIP_L$, followed immediately by restriction enzyme sites allowing for subcloning of desired target-protein-binding domains (e.g. peptides or protein domains). These SIP-fusions are then transfected into mammalian cells to eliminate by protein degradation specific target proteins which bind the subcloned peptides/protein domains by recruiting them into the ubiquitin conjugating complex.

The Parent SIP-vector (SIPpcDNA3.1) Cassette was Engineered as Follows

Oligonucleotides corresponding to the 5' and 3' end of $SIP_L$ were used in PCR to amplify the entire ORF of $SIP_L$ (SEQ ID NO:3). The forward primer contains a Hind III restriction site linker (5'-GATCAAGCTTATGGCTTCAGAAGAGCTACAG; (SEQ ID NO:46) restriction site is underlined) followed immediately by the $SIP_L$ (SEQ ID NO:3) start codon; the reverse primer contains an EcoRI restriction site and mutations in the stop codon allowing for translational readthrough (5'-GATCGAATTCtccAAATTCCGTGTCTCCTTTGGCTTG; (SEQ ID NO:47) mutated stop codon is in lowercase). The generated PCR product was then agarose gel-purified and digested with Hind III and EcoRI restriction enzymes (New England BioLabs; Beverly, Mass.). The product was again gel-purified before ligating into Hind III/EcoRI digested pcDNA3.1 expression vector (Invitrogen; Carlsbad, Calif.) with T4-DNA ligase (New England BioLabs). This construct was termed SIPpcDNA3.1.

For the construction of SIP-thioredoxin (Trx) peptide-aptamer fusions, clones from a peptide-aptamer library screened against Traf6 (see Table 4) were amplified by PCR with the following primers: Forward: 5'-CCTCTGAATTCCATATGAGCGATAAAATTATTCACC (SEQ ID NO:48) EcoRI underlined; Reverse: 5'-GATCCTCGAGTAGATGGCCAGCTAGGCCAGGTTA (SEQ ID NO:49) Xho I underlined.

The resulting PCR products (~350–370 bp) contain the ORF of thioredoxin (Trx) with the selected peptide aptamers inserted into its active-loop. The products were then digested with EcoRI and Xho I before ligating into the EcoRI/XhoI-digested SIPpcDNA3.1 cassette using T4-DNA ligase. Final clone constructs were numbered and were confirmed by sequencing before using in transfection studies.

Tranfection

Figure 10:
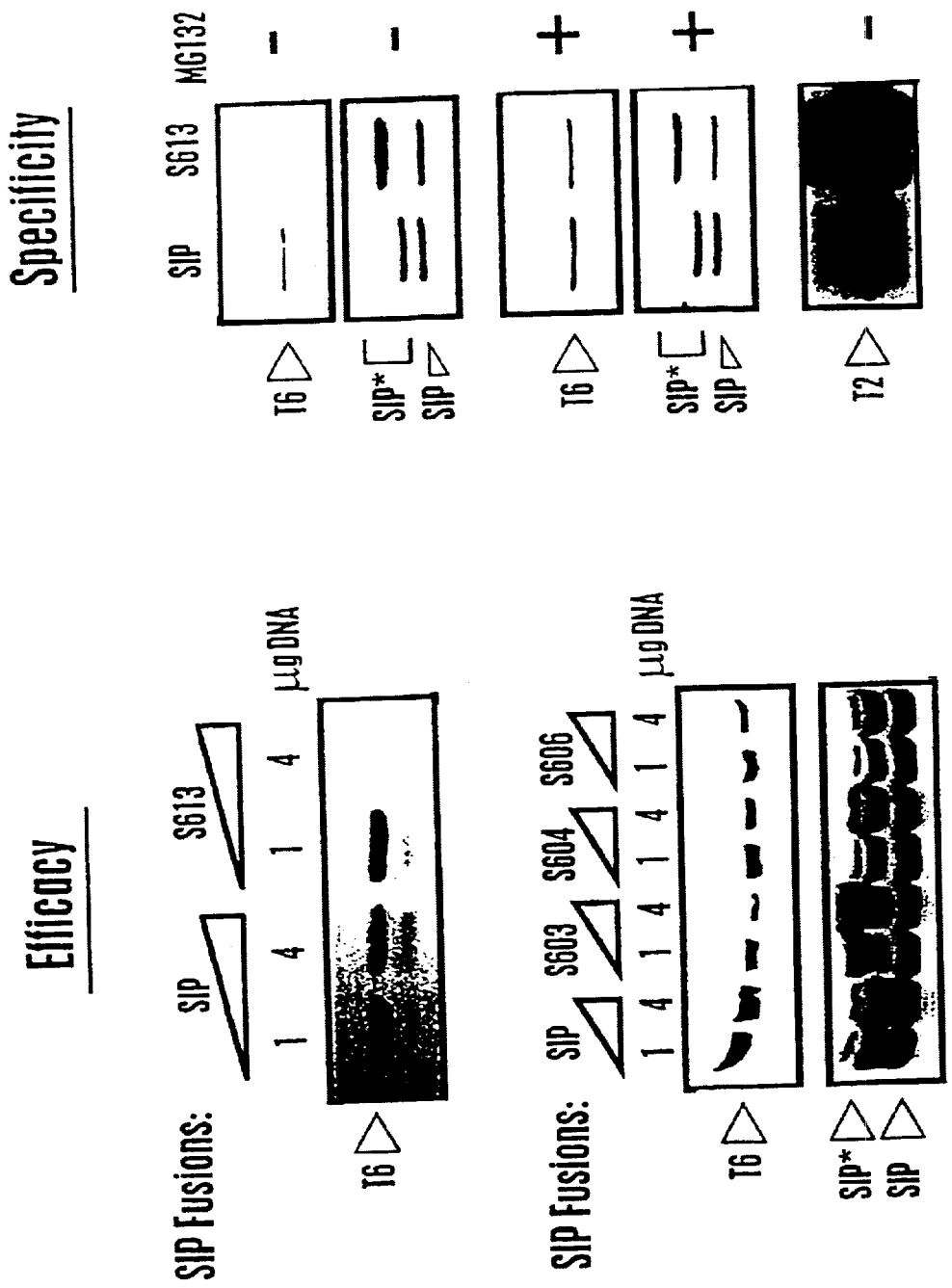
FIG. 10 shows the results of the SIP-mediated degradation of the target TRAF6 protein, set forth in Example 15.

HEK293T cells were transiently transfected by a lipofectamine method with various amounts (1 vs 4 µg) of pcDNA3 plasmids encoding either SIP-TR fusion protein lacking a TRAF6-binding peptide ("SIP") or SIP-TR fusion protein displaying one of the peptides shown in Table 4 above (set forth in FIG. 10 as S603, S604, S606). In some cases, the proteosome inhbitor MG132 (10 µM) was added to cultures to prevent protein turnover. SIP* in FIG. 10 corresponds to the control expression product of parental construct SIP pcDNA3.1.

To determine the efficacy of the SIP:TRAF-binding peptide chimeric proteins, levels of TRAF6 protein were then measured two days later by immunoblotting using a anti-TRAF6-specific antiserum (Santa Cruz Biotech, Inc.) in experiments where HEK293T cell lysates were normalized for total protein content (25 µg per lane). The cell lysates were analyzed by SDS-PAGE/immunoblotting using an enhanced chemiluminescence detection method, as described previously (Leo, et al. J Biol Chem, 274: 22414, 1999). The results shown in the left panel of FIG. 10 show that SIP-TR fusion proteins displaying TRAF6-binding peptides (S603, S604, and S613) induce a reduction in TRAF6 protein levels, with the S603 peptide representing the most potent of these.

To determine the specificity of the SIP:TRAF-binding peptide chimeric proteins, the same immunoblots were reprobed with an antiserum against SIP to demonstrate equivalent levels of production of SIP-TR fusion proteins, or with antibodies specific for TRAF2 to reveal selective degradation of TRAF6 but not TRAF2. The results shown in the right panel of FIG. 10 show that addition of a proteosome inhibitor, MG132, prevents the reductions in TRAF6. Note also that TRAF2 protein is not degraded, demonstrating the specificity of the targeting approach.

While the invention has been described in detail with reference to certain preferred embodiments thereof, it will be understood that modifications and variations are within the spirit and scope of that which is described and claimed.

Summary of Sequences

SEQ ID NO:1 is a cDNA (and the deduced amino acid sequence) encoding a Siah 1α of the present invention.

SEQ ID NO:2 is the deduced amino acid sequence of a Siah 1α protein of the present invention encoded by SEQ ID NO:1.

SEQ ID NO:3 is a cDNA (and the deduced amino acid sequence) encoding a human SIP-L polypeptide of the present invention.

SEQ ID NO:4 is the deduced amino acid sequence of a human SIP-L protein of the present invention encoded by SEQ ID NO:3.

SEQ ID NO:5 is a cDNA (and the deduced amino acid sequence) encoding a human SIP-S polypeptide of the present invention.

SEQ ID NO:6 is the deduced amino acid sequence of a human SIP-S protein of the present invention encoded by SEQ ID NO:5.

SEQ ID NO:7 is a cDNA (and the deduced amino acid sequence) encoding a human SAF-1α polypeptide of the present invention.

SEQ ID NO:8 is the deduced amino acid sequence of a SAF-1α protein of the present invention encoded by SEQ ID NO:7.

SEQ ID NO:9 is a cDNA (and the deduced amino acid sequence) encoding a human SAF-1β polypeptide of the present invention.

SEQ ID NO:10 is the deduced amino acid sequence of a SAF-1β protein encoded by SEQ ID NO:9.

SEQ ID NO:11 is a cDNA (and the deduced amino acid sequence) encoding a human SAF-2 polypeptide of the present invention.

SEQ ID NO:12 is the deduced amino acid sequence of a SAF-2 protein encoded by SEQ ID NO:11.

SEQ ID NO:13 is a cDNA (and the deduced amino acid sequence) encoding a human SAD polypeptide of the present invention.

SEQ ID NO:14 is the deduced amino acid sequence of a SAD protein encoded by SEQ ID NO:13.

That which is claimed is:

1. A method of inducing the degradation of the function of a target protein, said method comprising:

expressing, in a cell, a chimeric protein comprising a target-protein binding domain operatively linked to a protein-degradation binding domain of Siah-1, wherein following expression of said chimeric protein the function of the target protein bound by said target-protein binding domain is degraded.

2. The method of claim 1, wherein said cell is cultured.

3. The method of claim 1, wherein said cell is selected from the group consisting of a bacterial cell, yeast cell, mammalian cell, and insect cell.

4. The method of claim 3, wherein said cell is a bacterial cell.

5. The method of claim 3, wherein said cell is a yeast cell.

6. The method of claim 3, wherein said cell is a mammalian cell.

7. The method of claim 3, wherein said cell is a, and insect cell.

* * * * *

UNITED STATES PATENT AND TRADEMARK OFFICE
CERTIFICATE OF CORRECTION

PATENT NO. : 6,638,734 B1
DATED : October 28, 2003
INVENTOR(S) : Reed et al.

It is certified that error appears in the above-identified patent and that said Letters Patent is hereby corrected as shown below:

Column 80,
Line 31, please delete "a, and" and replace therefore with -- an --

Signed and Sealed this

Thirty-first Day of August, 2004

JON W. DUDAS
*Director of the United States Patent and Trademark Office*

SEQUENCE LISTING

```
<160> NUMBER OF SEQ ID NOS: 49

<210> SEQ ID NO 1
<211> LENGTH: 1274
<212> TYPE: DNA
<213> ORGANISM: Homo sapien
<220> FEATURE:
<221> NAME/KEY: CDS
<222> LOCATION: (274)...(1167)

<400> SEQUENCE: 1
tttctttagt tgtttatggt ccattttcta ttttagcatt tattattcta tgtagtctat      60
ccaaagacga ttaagggagt tccacatgtt ttccggaaca ttttgaaaag agagcttatc     120
cagtgtacag atcctaataa agtgcacatt cagtgtaatt ttattttttt aatatctttt     180
ttaatcctat ttttcttcct cttttgctca gtaaattttg tatgaaactt taaaggact      240 tatggcatgt aaacattatt tataaagtaa gtc atg gtt ata att att ttt ctc      294
                                    Met Val Ile Ile Ile Phe Leu
                                     1               5 ctg cct cct tat gta ttt att tca gaa atg agc cgt cag act gct aca      342
Leu Pro Pro Tyr Val Phe Ile Ser Glu Met Ser Arg Gln Thr Ala Thr
         10                  15                  20 gca tta cct acc ggt acc tcg aag tgt cca cca tcc cag agg gtg cct      390
Ala Leu Pro Thr Gly Thr Ser Lys Cys Pro Pro Ser Gln Arg Val Pro
 25                  30                  35 gcc ctg act ggc aca act gca tcc aac aat gac ttg gcg agt ctt ttt      438
Ala Leu Thr Gly Thr Thr Ala Ser Asn Asn Asp Leu Ala Ser Leu Phe
 40                  45                  50                  55 gag tgt cca gtc tgc ttt gac tat gtg tta ccg ccc att ctt caa tgt      486
Glu Cys Pro Val Cys Phe Asp Tyr Val Leu Pro Pro Ile Leu Gln Cys
                 60                  65                  70 cag agt ggc cat ctt gtt tgt agc aac tgt cgc cca aag ctc aca tgt      534
Gln Ser Gly His Leu Val Cys Ser Asn Cys Arg Pro Lys Leu Thr Cys
         75                  80                  85 tgt cca act tgc cgg ggc cct ttg gga tcc att cgc aac ttg gct atg      582
Cys Pro Thr Cys Arg Gly Pro Leu Gly Ser Ile Arg Asn Leu Ala Met
 90                  95                 100 gag aaa gtg gct aat tca gta ctt ttc ccc tgt aaa tat gcg tct tct      630
Glu Lys Val Ala Asn Ser Val Leu Phe Pro Cys Lys Tyr Ala Ser Ser
    105                 110                 115 gga tgt gaa ata act ctg cca cac aca gaa aaa gca gac cat gaa gag      678
Gly Cys Glu Ile Thr Leu Pro His Thr Glu Lys Ala Asp His Glu Glu
120                 125                 130                 135 ctc tgt gag ttt agg cct tat tcc tgt ccg tgc cct ggt gct tcc tgt      726
Leu Cys Glu Phe Arg Pro Tyr Ser Cys Pro Cys Pro Gly Ala Ser Cys
                140                 145                 150 aaa tgg caa ggc tct ctg gat gct gta atg ccc cat ctg atg cat cag      774
Lys Trp Gln Gly Ser Leu Asp Ala Val Met Pro His Leu Met His Gln
        155                 160                 165 cat aag tcc att aca acc cta cag gga gag gat ata gtt ttt ctt gct      822
His Lys Ser Ile Thr Thr Leu Gln Gly Glu Asp Ile Val Phe Leu Ala
        170                 175                 180 aca gac att aat ctt cct ggt gct gtt gac tgg gtg atg atg cag tcc      870
Thr Asp Ile Asn Leu Pro Gly Ala Val Asp Trp Val Met Met Gln Ser
```

```
Thr Asp Ile Asn Leu Pro Gly Ala Val Asp Trp Val Met Met Gln Ser
    185                 190                 195 tgt ttt ggc ttt cac ttc atg tta gtc tta gag aaa cag gaa aaa tac      918
Cys Phe Gly Phe His Phe Met Leu Val Leu Glu Lys Gln Glu Lys Tyr
200                 205                 210                 215 gat ggt cac cag cag ttc ttc gca atc gta cag ctg ata gga aca cgc      966
Asp Gly His Gln Gln Phe Phe Ala Ile Val Gln Leu Ile Gly Thr Arg
                220                 225                 230 aag caa gct gaa aat ttt gct tac cga ctt gag cta aat ggt cat agg     1014
Lys Gln Ala Glu Asn Phe Ala Tyr Arg Leu Glu Leu Asn Gly His Arg
            235                 240                 245 cga cga ttg act tgg gaa gcg act cct cga tct att cat gaa gga att     1062
Arg Arg Leu Thr Trp Glu Ala Thr Pro Arg Ser Ile His Glu Gly Ile
        250                 255                 260 gca aca gcc att atg aat agc gac tgt cta gtc ttt gac acc agc att     1110
Ala Thr Ala Ile Met Asn Ser Asp Cys Leu Val Phe Asp Thr Ser Ile
265                 270                 275 gca cag ctt ttt gca gaa aat ggc aat tta ggc atc aat gta act att     1158
Ala Gln Leu Phe Ala Glu Asn Gly Asn Leu Gly Ile Asn Val Thr Ile
280                 285                 290                 295 tcc atg tgt tgaaatggca atcaaacatt ttctggccag tgtttaaaac             1207
Ser Met Cys ttcagtttca cagaaaataa ggcacccatc tgtctgccaa cctaaaactc tttcggtagg   1267
tggaagc                                                             1274

<210> SEQ ID NO 2
<211> LENGTH: 298
<212> TYPE: PRT
<213> ORGANISM: Homo sapien

<400> SEQUENCE: 2

Met Val Ile Ile Ile Phe Leu Leu Pro Pro Tyr Val Phe Ile Ser Glu
1               5                   10                  15

Met Ser Arg Gln Thr Ala Thr Ala Leu Pro Thr Gly Thr Ser Lys Cys
            20                  25                  30

Pro Pro Ser Gln Arg Val Pro Ala Leu Thr Gly Thr Ala Ser Asn
        35                  40                  45

Asn Asp Leu Ala Ser Leu Phe Glu Cys Pro Val Cys Phe Asp Tyr Val
    50                  55                  60

Leu Pro Pro Ile Leu Gln Cys Gln Ser Gly His Leu Val Cys Ser Asn
65                  70                  75                  80

Cys Arg Pro Lys Leu Thr Cys Cys Pro Thr Cys Arg Gly Pro Leu Gly
                85                  90                  95

Ser Ile Arg Asn Leu Ala Met Glu Lys Val Ala Asn Ser Val Leu Phe
            100                 105                 110

Pro Cys Lys Tyr Ala Ser Ser Gly Cys Glu Ile Thr Leu Pro His Thr
        115                 120                 125

Glu Lys Ala Asp His Glu Glu Leu Cys Glu Phe Arg Pro Tyr Ser Cys
    130                 135                 140

Pro Cys Pro Gly Ala Ser Cys Lys Trp Gln Gly Ser Leu Asp Ala Val
145                 150                 155                 160

Met Pro His Leu Met His Gln His Lys Ser Ile Thr Thr Leu Gln Gly
                165                 170                 175

Glu Asp Ile Val Phe Leu Ala Thr Asp Ile Asn Leu Pro Gly Ala Val
            180                 185                 190

Asp Trp Val Met Met Gln Ser Cys Phe Gly Phe His Phe Met Leu Val
```

```
                    195                 200                     205
Leu Glu Lys Gln Glu Lys Tyr Asp Gly His Gln Gln Phe Phe Ala Ile
    210                 215                 220

Val Gln Leu Ile Gly Thr Arg Lys Gln Ala Glu Asn Phe Ala Tyr Arg
225                 230                 235                 240

Leu Glu Leu Asn Gly His Arg Arg Leu Thr Trp Glu Ala Thr Pro
                245                 250                 255

Arg Ser Ile His Glu Gly Ile Ala Thr Ala Ile Met Asn Ser Asp Cys
                260                 265                 270

Leu Val Phe Asp Thr Ser Ile Ala Gln Leu Phe Ala Glu Asn Gly Asn
                275                 280                 285

Leu Gly Ile Asn Val Thr Ile Ser Met Cys
    290                 295

<210> SEQ ID NO 3
<211> LENGTH: 1432
<212> TYPE: DNA
<213> ORGANISM: Homo sapien
<220> FEATURE:
<221> NAME/KEY: CDS
<222> LOCATION: (25)...(708)

<400> SEQUENCE: 3
ggacttcggc ctgacccagc cccc atg gct tca gaa gag cta cag aaa gat        51
                           Met Ala Ser Glu Glu Leu Gln Lys Asp
                            1               5 cta gaa gag gta aag gtg ttg ctg gaa aag gct act agg aaa aga gta       99
Leu Glu Glu Val Lys Val Leu Leu Glu Lys Ala Thr Arg Lys Arg Val
 10              15                  20                  25 cgt gat gcc ctt aca gct gaa aaa tcc aag att gag aca gaa atc aag     147
Arg Asp Ala Leu Thr Ala Glu Lys Ser Lys Ile Glu Thr Glu Ile Lys
                30                  35                  40 aac aag atg caa cag aaa tca cag aag aaa gca gaa ctt ctt gat aat     195
Asn Lys Met Gln Gln Lys Ser Gln Lys Lys Ala Glu Leu Leu Asp Asn
            45                  50                  55 gaa aaa cca gct gct gtg gtt gct ccc att aca acg ggc tat acg gtg     243
Glu Lys Pro Ala Ala Val Val Ala Pro Ile Thr Thr Gly Tyr Thr Val
        60                  65                  70 aaa atc agt aat tat gga tgg gat cag tca gat aag ttt gtg aaa atc     291
Lys Ile Ser Asn Tyr Gly Trp Asp Gln Ser Asp Lys Phe Val Lys Ile
    75                  80                  85 tac att acc tta act gga gtt cat caa gtt ccc act gag aat gtg cag     339
Tyr Ile Thr Leu Thr Gly Val His Gln Val Pro Thr Glu Asn Val Gln
 90              95                  100                 105 gtg cat ttc aca gag agg tca ttt gat ctt ttg gta aag aat cta aat     387
Val His Phe Thr Glu Arg Ser Phe Asp Leu Leu Val Lys Asn Leu Asn
                110                 115                 120 ggg aag agt tac tcc atg att gtg aac aat ctc ttg aaa ccc atc tct     435
Gly Lys Ser Tyr Ser Met Ile Val Asn Asn Leu Leu Lys Pro Ile Ser
            125                 130                 135 gtg gaa ggc agt tca aaa aaa gtc aag act gat aca gtt ctt ata ttg     483
Val Glu Gly Ser Ser Lys Lys Val Lys Thr Asp Thr Val Leu Ile Leu
        140                 145                 150 tgt aga aag aaa gtg gaa aac aca agg tgg gat tac ctg acc cag gtt     531
Cys Arg Lys Lys Val Glu Asn Thr Arg Trp Asp Tyr Leu Thr Gln Val
    155                 160                 165 gaa aag gag tgc aaa gaa aaa gag aag ccc tcc tat gac act gaa aca     579
Glu Lys Glu Cys Lys Glu Lys Glu Lys Pro Ser Tyr Asp Thr Glu Thr
170                 175                 180                 185
```

-continued

```
gat cct agt gag gga ttg atg aat gtt cta aag aaa att tat gaa gat      627
Asp Pro Ser Glu Gly Leu Met Asn Val Leu Lys Lys Ile Tyr Glu Asp
            190                 195                 200 gga gac gat gat atg aag cga acc att aat aaa gcc tgg gtg gaa tca      675
Gly Asp Asp Asp Met Lys Arg Thr Ile Asn Lys Ala Trp Val Glu Ser
        205                 210                 215 aga gag aag caa gcc aaa gga gac acg gaa ttt tgagacttta aagtcgtttt    728
Arg Glu Lys Gln Ala Lys Gly Asp Thr Glu Phe
220                 225 gggaactgtg atgtgatgtg aaatactga tgtttccagt aagggaatat tggtgagctg     788
catatataaa tttgacagat agctatttac atagccttct aagtaaaggc aatgaattct    848
ccatttccta ctggaggatt tatttaaata aaatatgctt attaaacact cctgcaaaga    908
tggttttatt agtaccctgg tcattttgtt caaggaaggg ttatattgca ttctcacgtg    968
aaatataaaa agcaagtctt gcccaataaa acgctacat tgtgtgtatt ttttgttcag     1028
ctaagaattg gaaagtatt tgcttgcctt ttaagttact gacatcagct tccaccagtg     1088
taaaaattga gtaaaacctg aagttttgca taaaatgcaa atcggtgcct gtgcttgaag    1148
gttgctgtag agcatctgac cccttattac caccttaagc aatgtatatg ccatgcatta    1208
ccatgcacta attcaatcac aggtgtttct atctagattt aaatatattt gtcaatgaat    1268
gtggaataga aatctaaac atgacaataa tagacatatc tttgtatggt accagttagt     1328
tttgccgtgg atcagatggt ttataaaagt aataaccata aagcaaaaaa taatttgaaa    1388
gcccgtctat tcctatgctc aataaagtta agttttctt catt                      1432
```

<210> SEQ ID NO 4
<211> LENGTH: 228
<212> TYPE: PRT
<213> ORGANISM: Homo sapien

<400> SEQUENCE: 4

```
Met Ala Ser Glu Glu Leu Gln Lys Asp Leu Glu Glu Val Lys Val Leu
  1               5                  10                  15

Leu Glu Lys Ala Thr Arg Lys Arg Val Arg Asp Ala Leu Thr Ala Glu
                 20                  25                  30

Lys Ser Lys Ile Glu Thr Glu Ile Lys Asn Lys Met Gln Gln Lys Ser
             35                  40                  45

Gln Lys Lys Ala Glu Leu Leu Asp Asn Glu Lys Pro Ala Ala Val Val
         50                  55                  60

Ala Pro Ile Thr Thr Gly Tyr Thr Val Lys Ile Ser Asn Tyr Gly Trp
 65                  70                  75                  80

Asp Gln Ser Asp Lys Phe Val Lys Ile Tyr Ile Thr Leu Thr Gly Val
                 85                  90                  95

His Gln Val Pro Thr Glu Asn Val Gln Val His Phe Thr Glu Arg Ser
                100                 105                 110

Phe Asp Leu Leu Val Lys Asn Leu Asn Gly Lys Ser Tyr Ser Met Ile
            115                 120                 125

Val Asn Asn Leu Leu Lys Pro Ile Ser Val Glu Gly Ser Ser Lys Lys
        130                 135                 140

Val Lys Thr Asp Thr Val Leu Ile Leu Cys Arg Lys Lys Val Glu Asn
145                 150                 155                 160

Thr Arg Trp Asp Tyr Leu Thr Gln Val Glu Lys Glu Cys Lys Glu Lys
                165                 170                 175

Glu Lys Pro Ser Tyr Asp Thr Glu Thr Asp Pro Ser Glu Gly Leu Met
            180                 185                 190
```

```
Asn Val Leu Lys Lys Ile Tyr Glu Asp Gly Asp Asp Met Lys Arg
        195                 200                 205

Thr Ile Asn Lys Ala Trp Val Glu Ser Arg Glu Lys Gln Ala Lys Gly
    210                 215                 220

Asp Thr Glu Phe
225

<210> SEQ ID NO 5
<211> LENGTH: 1413
<212> TYPE: DNA
<213> ORGANISM: Homo sapien
<220> FEATURE:
<221> NAME/KEY: CDS
<222> LOCATION: (25)...(264)

<400> SEQUENCE: 5
ggacttcggc ctgacccagc cccc atg gct tca gaa gag cta cag aaa gat          51
                          Met Ala Ser Glu Glu Leu Gln Lys Asp
                            1               5 cta gaa gag gta aag gtg ttg ctg gaa aag gct act agg aaa aga gta        99
Leu Glu Glu Val Lys Val Leu Leu Glu Lys Ala Thr Arg Lys Arg Val
 10                  15                  20                  25 cgt gat gcc ctt aca gct gaa aaa tcc aag att gag aca gaa atc aag       147
Arg Asp Ala Leu Thr Ala Glu Lys Ser Lys Ile Glu Thr Glu Ile Lys
                 30                  35                  40 aac aag atg caa cag aaa tca cag aag aaa gca gaa ctt ctt gat aat       195
Asn Lys Met Gln Gln Lys Ser Gln Lys Lys Ala Glu Leu Leu Asp Asn
             45                  50                  55 gaa aaa cca gct gct gtg gtt gct ccc att aca acg ggc tat acg gat       243
Glu Lys Pro Ala Ala Val Val Ala Pro Ile Thr Thr Gly Tyr Thr Asp
         60                  65                  70 ggg atc agt cag ata agt ttg tgaaaatcta cattaccta actggagttc           294
Gly Ile Ser Gln Ile Ser Leu
     75                  80 atcaagttcc cactgagaat gtgcaggtgc atttcacaga gaggtcattt gatcttttgg     354
taaagaatct aaatgggaag agttactcca tgattgtgaa caatctcttg aaacccatct    414
ctgtggaagg cagttcaaaa aaagtcaaga ctgatacagt tcttatattg tgtagaaaga    474
aagtggaaaa cacaaggtgg gattacctga cccaggttga aaaggagtgc aaagaaaaag    534
agaagccctc ctatgacact gaaacagatc ctagtgaggg attgatgaat gttctaaaga    594
aaatttatga agatggagac gatgatatga agcgaaccat taataaagcc tgggtggaat    654
caagagagaa gcaagccaaa ggagacacgg aattttgaga ctttaaagtc gttttgggaa    714
ctgtgatgtg atgtggaaat actgatgttt ccagtaagga aatattggtg agctgcatat    774
ataaatttga cagatagcta tttacatagc cttctaagta aaggcaatga attctccatt    834
tcctactgga ggatttattt aaataaaata tgcttattaa acactcctgc aaagatggtt    894
ttattagtac cctggtcatt ttgttcaagg aagggttata ttgcattctc acgtgaaata    954
taaaaagcaa gtcttgccca ataaaaacgc tacattgtgt gtatttttg ttcagctaag    1014 aattggaaaa gtatttgctt gccttttaag ttactgacat cagcttccac cagtgtaaaa   1074
attgagtaaa acctgaagtt ttgcataaaa tgcaaatcgg tgcctgtgct tgaaggttgc   1134
tgtagagcat ctgaccccct tattaccacct taagcaatgt atatgccatg cattaccatg   1194
cactaattca atcacaggtg tttctatcta gatttaaata tatttgtcaa tgaatgtgga   1254
atagaaaatc taaacatgac aataatagac atatctttgt atggtaccag ttagttttgc   1314
```

```
cgtggatcag atggtttata aaagtaataa ccataaagca aaaaataatt tgaaagcccg   1374
tctattccta tgctcaataa agttaagttt ttcttcatt                         1413
```

<210> SEQ ID NO 6
<211> LENGTH: 80
<212> TYPE: PRT
<213> ORGANISM: Homo sapien

<400> SEQUENCE: 6

```
Met Ala Ser Glu Glu Leu Gln Lys Asp Leu Glu Glu Val Lys Val Leu
 1               5                  10                  15

Leu Glu Lys Ala Thr Arg Lys Arg Val Arg Asp Ala Leu Thr Ala Glu
            20                  25                  30

Lys Ser Lys Ile Glu Thr Glu Ile Lys Asn Lys Met Gln Gln Lys Ser
        35                  40                  45

Gln Lys Lys Ala Glu Leu Leu Asp Asn Glu Lys Pro Ala Ala Val Val
    50                  55                  60

Ala Pro Ile Thr Thr Gly Tyr Thr Asp Gly Ile Ser Gln Ile Ser Leu
65                  70                  75                  80
```

<210> SEQ ID NO 7
<211> LENGTH: 1673
<212> TYPE: DNA
<213> ORGANISM: Homo sapien
<220> FEATURE:
<221> NAME/KEY: CDS
<222> LOCATION: (61)...(1389)

<400> SEQUENCE: 7

```
ccggagggtg caggcgacgg gaagcgcggg tggtcggctg ggtccggct cctggagaac    60 atg gcc cgg cct ccc ggg ggc tct ggt ccc ctc ctc gat tca gag cat   108
Met Ala Arg Pro Pro Gly Gly Ser Gly Pro Leu Leu Asp Ser Glu His
 1               5                  10                  15 tct tca ctc cag aat aat gag caa ccc tct ttg gcc acc agc tcc aat   156
Ser Ser Leu Gln Asn Asn Glu Gln Pro Ser Leu Ala Thr Ser Ser Asn
            20                  25                  30 cag act agc atg cag gat gaa caa cca agt gat tca ttc caa gga cag   204
Gln Thr Ser Met Gln Asp Glu Gln Pro Ser Asp Ser Phe Gln Gly Gln
        35                  40                  45 gca gcc cag tct ggt gtt tgg aat gac gac agt atg tta ggg cct agt   252
Ala Ala Gln Ser Gly Val Trp Asn Asp Asp Ser Met Leu Gly Pro Ser
    50                  55                  60 caa aat ttt gaa gct gag tca att caa gat aat gcg cat atg gca gag   300
Gln Asn Phe Glu Ala Glu Ser Ile Gln Asp Asn Ala His Met Ala Glu
65                  70                  75                  80 ggc aca ggt ttc tat ccc tca gaa ccc atg ctc tgt agt gaa tcg gtg   348
Gly Thr Gly Phe Tyr Pro Ser Glu Pro Met Leu Cys Ser Glu Ser Val
                85                  90                  95 gaa ggg caa gtg cca cat tca tta gag acc ttg tat caa tca gct gac   396
Glu Gly Gln Val Pro His Ser Leu Glu Thr Leu Tyr Gln Ser Ala Asp
           100                 105                 110 tgt tct gat gcc aat gat gcc ttg ata gtg tta ata cat ctt ctc atg   444
Cys Ser Asp Ala Asn Asp Ala Leu Ile Val Leu Ile His Leu Leu Met
       115                 120                 125 ttg gag tca ggt tac ata cct cag ggc acc gaa gcc aaa gca ctg tcc   492
Leu Glu Ser Gly Tyr Ile Pro Gln Gly Thr Glu Ala Lys Ala Leu Ser
   130                 135                 140 atg ccg gag aag tgg aag ttg agc ggg gtg tat aag ctg cag tac atg   540
Met Pro Glu Lys Trp Lys Leu Ser Gly Val Tyr Lys Leu Gln Tyr Met
145                 150                 155                 160
```

```
cat cct ctc tgc gag ggc agc tcc gct act ctc acc tgt gtg cct ttg      588
His Pro Leu Cys Glu Gly Ser Ser Ala Thr Leu Thr Cys Val Pro Leu
            165                 170                 175 gga aac ctg att gtt gta aat gct aca cta aaa atc aac aat gag att      636
Gly Asn Leu Ile Val Val Asn Ala Thr Leu Lys Ile Asn Asn Glu Ile
        180                 185                 190 aga agt gtg aaa aga ttg cag ctg cta cca aaa tct ttt att tgc aaa      684
Arg Ser Val Lys Arg Leu Gln Leu Leu Pro Lys Ser Phe Ile Cys Lys
    195                 200                 205 gag aaa cta ggg gaa aat gta gcc aac ata tac aaa gat ctt cag aaa      732
Glu Lys Leu Gly Glu Asn Val Ala Asn Ile Tyr Lys Asp Leu Gln Lys
210                 215                 220 ctc tct cgc ctc ttt aaa gac cag ctg gtg tat cct ctt ctg gct ttt      780
Leu Ser Arg Leu Phe Lys Asp Gln Leu Val Tyr Pro Leu Leu Ala Phe
225                 230                 235                 240 acc cga caa gca ctg aac cta cca gat gta ttt ggg ttg gtc gtc ctc      828
Thr Arg Gln Ala Leu Asn Leu Pro Asp Val Phe Gly Leu Val Val Leu
                245                 250                 255 cca ttg gaa ctg aaa cta cgg atc ttc cga ctt ctg gat gtt cgt tcc      876
Pro Leu Glu Leu Lys Leu Arg Ile Phe Arg Leu Leu Asp Val Arg Ser
            260                 265                 270 gtc ttg tct ttg tct gcg gtt tgt cgt gac ctc ttt act gct tca aat      924
Val Leu Ser Leu Ser Ala Val Cys Arg Asp Leu Phe Thr Ala Ser Asn
        275                 280                 285 gac cca ctc ctg tgg agg ttt tta tat ctg cgt gat ttt cga gac aat      972
Asp Pro Leu Leu Trp Arg Phe Leu Tyr Leu Arg Asp Phe Arg Asp Asn
    290                 295                 300 act gtc aga gtt caa gac aca gat tgg aaa gaa ctg tac agg aag agg     1020
Thr Val Arg Val Gln Asp Thr Asp Trp Lys Glu Leu Tyr Arg Lys Arg
305                 310                 315                 320 cac ata caa aga aaa gaa tcc ccg aaa ggg cgg ttt gtg atg ctc ctg     1068
His Ile Gln Arg Lys Glu Ser Pro Lys Gly Arg Phe Val Met Leu Leu
                325                 330                 335 cca tcg tca act cac acc att cca ttc tat ccc aac ccc ttg cac cct     1116
Pro Ser Ser Thr His Thr Ile Pro Phe Tyr Pro Asn Pro Leu His Pro
            340                 345                 350 agg cca ttt cct agc tcc cgc ctt cct cca gga att atc ggg ggt gaa     1164
Arg Pro Phe Pro Ser Ser Arg Leu Pro Pro Gly Ile Ile Gly Gly Glu
        355                 360                 365 tat gac caa aga cca aca ctt ccc tat gtt gga gac cca atc agt tca     1212
Tyr Asp Gln Arg Pro Thr Leu Pro Tyr Val Gly Asp Pro Ile Ser Ser
    370                 375                 380 ctc att cct ggt cct ggg gag acg ccc agc cag ttt cct cca ctg aga     1260
Leu Ile Pro Gly Pro Gly Glu Thr Pro Ser Gln Phe Pro Pro Leu Arg
385                 390                 395                 400 cca cgc ttt gat cca gtt ggc cca ctt cca gga cct aac ccc atc ttg     1308
Pro Arg Phe Asp Pro Val Gly Pro Leu Pro Gly Pro Asn Pro Ile Leu
                405                 410                 415 cca ggg cga ggc ggc ccc aat gac aga ttt ccc ttt aga ccc agc agg     1356
Pro Gly Arg Gly Gly Pro Asn Asp Arg Phe Pro Phe Arg Pro Ser Arg
            420                 425                 430 ggt cgg cca act gat ggc cgg ctg tca ttc atg tgattgattt gtaatttcat   1409
Gly Arg Pro Thr Asp Gly Arg Leu Ser Phe Met
        435                 440 ttctggagct ccatttgttt tgtttctaa actacagatg tcaactcctt ggggtgctga    1469
tctcgagtgt tattttctga ttgtggtgtt gagagttgca ctcccagaaa cctttaaga    1529 gatacattta tagccctagg ggtggtatga cccaaaggtt cctctgtgac aaggttggcc   1589
```

```
ttgggaatag ttggctgcca atctccctgc tcttggttct cctctagatt gaagtttgtt   1649
ttctgatgct gttcttacca gatt                                          1673
```

<210> SEQ ID NO 8
<211> LENGTH: 443
<212> TYPE: PRT
<213> ORGANISM: Homo sapien

<400> SEQUENCE: 8

```
Met Ala Arg Pro Pro Gly Gly Ser Gly Pro Leu Leu Asp Ser Glu His
 1               5                  10                  15

Ser Ser Leu Gln Asn Asn Glu Gln Pro Ser Leu Ala Thr Ser Ser Asn
            20                  25                  30

Gln Thr Ser Met Gln Asp Glu Gln Pro Ser Asp Ser Phe Gln Gly Gln
        35                  40                  45

Ala Ala Gln Ser Gly Val Trp Asn Asp Asp Ser Met Leu Gly Pro Ser
    50                  55                  60

Gln Asn Phe Glu Ala Glu Ser Ile Gln Asp Asn Ala His Met Ala Glu
65                  70                  75                  80

Gly Thr Gly Phe Tyr Pro Ser Glu Pro Met Leu Cys Ser Glu Ser Val
                85                  90                  95

Glu Gly Gln Val Pro His Ser Leu Glu Thr Leu Tyr Gln Ser Ala Asp
            100                 105                 110

Cys Ser Asp Ala Asn Asp Ala Leu Ile Val Leu Ile His Leu Leu Met
        115                 120                 125

Leu Glu Ser Gly Tyr Ile Pro Gln Gly Thr Glu Ala Lys Ala Leu Ser
    130                 135                 140

Met Pro Glu Lys Trp Lys Leu Ser Gly Val Tyr Lys Leu Gln Tyr Met
145                 150                 155                 160

His Pro Leu Cys Glu Gly Ser Ser Ala Thr Leu Thr Cys Val Pro Leu
                165                 170                 175

Gly Asn Leu Ile Val Val Asn Ala Thr Leu Lys Ile Asn Asn Glu Ile
            180                 185                 190

Arg Ser Val Lys Arg Leu Gln Leu Leu Pro Lys Ser Phe Ile Cys Lys
        195                 200                 205

Glu Lys Leu Gly Glu Asn Val Ala Asn Ile Tyr Lys Asp Leu Gln Lys
    210                 215                 220

Leu Ser Arg Leu Phe Lys Asp Gln Leu Val Tyr Pro Leu Leu Ala Phe
225                 230                 235                 240

Thr Arg Gln Ala Leu Asn Leu Pro Asp Val Phe Gly Leu Val Val Leu
                245                 250                 255

Pro Leu Glu Leu Lys Leu Arg Ile Phe Arg Leu Leu Asp Val Arg Ser
            260                 265                 270

Val Leu Ser Leu Ser Ala Val Cys Arg Asp Leu Phe Thr Ala Ser Asn
        275                 280                 285

Asp Pro Leu Leu Trp Arg Phe Leu Tyr Leu Arg Asp Phe Arg Asp Asn
    290                 295                 300

Thr Val Arg Val Gln Asp Thr Asp Trp Lys Glu Leu Tyr Arg Lys Arg
305                 310                 315                 320

His Ile Gln Arg Lys Glu Ser Pro Lys Gly Arg Phe Val Met Leu Leu
                325                 330                 335

Pro Ser Ser Thr His Thr Ile Pro Phe Tyr Pro Asn Pro Leu His Pro
            340                 345                 350

Arg Pro Phe Pro Ser Ser Arg Leu Pro Pro Gly Ile Ile Gly Gly Glu
```

-continued

```
               355                 360                 365
Tyr Asp Gln Arg Pro Thr Leu Pro Tyr Val Gly Asp Pro Ile Ser Ser
    370                 375                 380

Leu Ile Pro Gly Pro Gly Glu Thr Pro Ser Gln Phe Pro Pro Leu Arg
385                 390                 395                 400

Pro Arg Phe Asp Pro Val Gly Pro Leu Pro Gly Pro Asn Pro Ile Leu
                405                 410                 415

Pro Gly Arg Gly Gly Pro Asn Asp Arg Phe Pro Phe Arg Pro Ser Arg
            420                 425                 430

Gly Arg Pro Thr Asp Gly Arg Leu Ser Phe Met
        435                 440

<210> SEQ ID NO 9
<211> LENGTH: 1892
<212> TYPE: DNA
<213> ORGANISM: Homo sapien
<220> FEATURE:
<221> NAME/KEY: CDS
<222> LOCATION: (43)...(1608)

<400> SEQUENCE: 9
gccgcttccg ggtccaggcc cctcgggccg cctgccgccg tc atg agg ctg cgg        54
                                              Met Arg Leu Arg
                                              1 gtg cgg ctt ctg aag cgg acc tgg ccg ctg gag gtg ccc gag acg gag      102
Val Arg Leu Leu Lys Arg Thr Trp Pro Leu Glu Val Pro Glu Thr Glu
 5                  10                  15                  20 ccg acg ctg ggg cat ttg cgc tcg cac ctg agg cag tcc ctg ctg tgc      150
Pro Thr Leu Gly His Leu Arg Ser His Leu Arg Gln Ser Leu Leu Cys
                25                  30                  35 acc tgg ggg tac agt tct aat acc cga ttt aca att aca ttg aac tac      198
Thr Trp Gly Tyr Ser Ser Asn Thr Arg Phe Thr Ile Thr Leu Asn Tyr
            40                  45                  50 aag gat ccc ctc act gga gat gaa gag acc ttg gct tca tat ggg att      246
Lys Asp Pro Leu Thr Gly Asp Glu Glu Thr Leu Ala Ser Tyr Gly Ile
        55                  60                  65 gtt tct ggg gac ttg ata tgt ttg att ctt caa gat gac att cca gcg      294
Val Ser Gly Asp Leu Ile Cys Leu Ile Leu Gln Asp Asp Ile Pro Ala
    70                  75                  80 cct aat ata cct tca tcc aca gat tca gag cat tct tca ctc cag aat      342
Pro Asn Ile Pro Ser Ser Thr Asp Ser Glu His Ser Ser Leu Gln Asn
85                  90                  95                  100 aat gag caa ccc tct ttg gcc acc agc tcc aat cag act agc atg cag      390
Asn Glu Gln Pro Ser Leu Ala Thr Ser Ser Asn Gln Thr Ser Met Gln
                105                 110                 115 gat gaa caa cca agt gat tca ttc caa gga cag gca gcc cag tct ggt      438
Asp Glu Gln Pro Ser Asp Ser Phe Gln Gly Gln Ala Ala Gln Ser Gly
            120                 125                 130 gtt tgg aat gac gac agt atg tta ggg cct agt caa aat ttt gaa gct      486
Val Trp Asn Asp Asp Ser Met Leu Gly Pro Ser Gln Asn Phe Glu Ala
        135                 140                 145 gag tca att caa gat aat gcg cat atg gca gag ggc aca ggt ttc tat      534
Glu Ser Ile Gln Asp Asn Ala His Met Ala Glu Gly Thr Gly Phe Tyr
    150                 155                 160 ccc tca gaa ccc atg ctc tgt agt gaa tcg gtg gaa ggg caa gtg cca      582
Pro Ser Glu Pro Met Leu Cys Ser Glu Ser Val Glu Gly Gln Val Pro
165                 170                 175                 180 cat tca tta gag acc ttg tat caa tca gct gac tgt tct gat gcc aat      630
His Ser Leu Glu Thr Leu Tyr Gln Ser Ala Asp Cys Ser Asp Ala Asn
                185                 190                 195
```

```
gat gcc ttg ata gtg ttg ata cat ctt ctc atg ttg gag tca ggt tac      678
Asp Ala Leu Ile Val Leu Ile His Leu Leu Met Leu Glu Ser Gly Tyr
            200                 205                 210 ata cct cag ggc acc gaa gcc aaa gca ctg tcc atg ccg gag aag tgg      726
Ile Pro Gln Gly Thr Glu Ala Lys Ala Leu Ser Met Pro Glu Lys Trp
            215                 220                 225 aag ttg agc ggg gtg tat aag ctg cag tac atg cat cct ctc tgc gag      774
Lys Leu Ser Gly Val Tyr Lys Leu Gln Tyr Met His Pro Leu Cys Glu
            230                 235                 240 ggc agc tcc gct act ctc acc tgt gtg cct ttg gga aac ctg att gtt      822
Gly Ser Ser Ala Thr Leu Thr Cys Val Pro Leu Gly Asn Leu Ile Val
245                 250                 255                 260 gta aat gct aca cta aaa atc aac aat gag att aga agt gtg aaa aga      870
Val Asn Ala Thr Leu Lys Ile Asn Asn Glu Ile Arg Ser Val Lys Arg
                265                 270                 275 ttg cag ctg cta cca aaa tct ttt att tgc aaa gag aaa cta ggg gaa      918
Leu Gln Leu Leu Pro Lys Ser Phe Ile Cys Lys Glu Lys Leu Gly Glu
            280                 285                 290 aat gta gcc aac ata tac aaa gat ctt cag aaa ctc tct cgc ctc ttt      966
Asn Val Ala Asn Ile Tyr Lys Asp Leu Gln Lys Leu Ser Arg Leu Phe
            295                 300                 305 aaa gac cag ctg gtg tat cct ctt ctg gct ttt acc cga caa gca ctg     1014
Lys Asp Gln Leu Val Tyr Pro Leu Leu Ala Phe Thr Arg Gln Ala Leu
310                 315                 320 aac cta cca gat gta ttt ggg ttg gtc gtc ctc cca ttg gaa ctg aaa     1062
Asn Leu Pro Asp Val Phe Gly Leu Val Val Leu Pro Leu Glu Leu Lys
325                 330                 335                 340 cta cgg atc ttc cga ctt ctg gat gtt cgt tcc gtc ttg tct ttg tct     1110
Leu Arg Ile Phe Arg Leu Leu Asp Val Arg Ser Val Leu Ser Leu Ser
                345                 350                 355 gcg gtt tgt cgt gac ctc ttt act gct tca aat gac cca ctc ctg tgg     1158
Ala Val Cys Arg Asp Leu Phe Thr Ala Ser Asn Asp Pro Leu Leu Trp
            360                 365                 370 agg ttt tta tat ctg cgt gat ttt cga gac aat act gtc aga gtt caa     1206
Arg Phe Leu Tyr Leu Arg Asp Phe Arg Asp Asn Thr Val Arg Val Gln
    375                 380                 385 gac aca gat tgg aaa gaa ctg tac agg aag agg cac ata caa aga aaa     1254
Asp Thr Asp Trp Lys Glu Leu Tyr Arg Lys Arg His Ile Gln Arg Lys
390                 395                 400 gaa tcc ccg aaa ggg cgg ttt gtg atg ctc ctg cca tcg tca act cac     1302
Glu Ser Pro Lys Gly Arg Phe Val Met Leu Leu Pro Ser Ser Thr His
405                 410                 415                 420 acc att cca ttc tat ccc aac ccc ttg cac cct agg cca ttt cct agc     1350
Thr Ile Pro Phe Tyr Pro Asn Pro Leu His Pro Arg Pro Phe Pro Ser
                425                 430                 435 tcc cgc ctt cct cca gga att atc ggg ggt gaa tat gac caa aga cca     1398
Ser Arg Leu Pro Pro Gly Ile Ile Gly Gly Glu Tyr Asp Gln Arg Pro
            440                 445                 450 aca ctt ccc tat gtt gga gac cca atc agt tca ctc att cct ggt cct     1446
Thr Leu Pro Tyr Val Gly Asp Pro Ile Ser Ser Leu Ile Pro Gly Pro
            455                 460                 465 ggg gag acg ccc agc cag ttt cct cca ctg aga cca cgc ttt gat cca     1494
Gly Glu Thr Pro Ser Gln Phe Pro Pro Leu Arg Pro Arg Phe Asp Pro
470                 475                 480 gtt ggc cca ctt cca gga cct aac ccc atc ttg cca ggg cga ggc ggc     1542
Val Gly Pro Leu Pro Gly Pro Asn Pro Ile Leu Pro Gly Arg Gly Gly
485                 490                 495                 500 ccc aat gac aga ttt ccc ttt aga ccc agc agg ggt cgg cca act gat     1590
Pro Asn Asp Arg Phe Pro Phe Arg Pro Ser Arg Gly Arg Pro Thr Asp
```

```
                    505                 510                 515
ggc cgg ctg tca ttc atg tgattgattt gtaatttcat ttctggagct              1638
Gly Arg Leu Ser Phe Met
            520 ccatttgttt ttgtttctaa actacagatg tcaactcctt ggggtgctga tctcgagtgt     1698 tattttctga ttgtggtgtt gagagttgca ctcccagaaa ccttttaaga gatacattta    1758 tagccctagg ggtggtatga cccaaaggtt cctctgtgac aaggttggcc ttgggaatag    1818 ttggctgcca atctccctgc tcttggttct cctctagatt gaagtttgtt ttctgatgct    1878 gttcttacca gatt                                                       1892

<210> SEQ ID NO 10
<211> LENGTH: 522
<212> TYPE: PRT
<213> ORGANISM: Homo sapien

<400> SEQUENCE: 10

Met Arg Leu Arg Val Arg Leu Leu Lys Arg Thr Trp Pro Leu Glu Val
 1               5                  10                  15

Pro Glu Thr Glu Pro Thr Leu Gly His Leu Arg Ser His Leu Arg Gln
                20                  25                  30

Ser Leu Leu Cys Thr Trp Gly Tyr Ser Ser Asn Thr Arg Phe Thr Ile
            35                  40                  45

Thr Leu Asn Tyr Lys Asp Pro Leu Thr Gly Asp Glu Glu Thr Leu Ala
        50                  55                  60

Ser Tyr Gly Ile Val Ser Gly Asp Leu Ile Cys Leu Ile Leu Gln Asp
65                  70                  75                  80

Asp Ile Pro Ala Pro Asn Ile Pro Ser Ser Thr Asp Ser Glu His Ser
                85                  90                  95

Ser Leu Gln Asn Asn Glu Gln Pro Ser Leu Ala Thr Ser Ser Asn Gln
            100                 105                 110

Thr Ser Met Gln Asp Glu Gln Pro Ser Asp Ser Phe Gln Gly Gln Ala
        115                 120                 125

Ala Gln Ser Gly Val Trp Asn Asp Asp Ser Met Leu Gly Pro Ser Gln
    130                 135                 140

Asn Phe Glu Ala Glu Ser Ile Gln Asp Asn Ala His Met Ala Glu Gly
145                 150                 155                 160

Thr Gly Phe Tyr Pro Ser Glu Pro Met Leu Cys Ser Glu Ser Val Glu
                165                 170                 175

Gly Gln Val Pro His Ser Leu Glu Thr Leu Tyr Gln Ser Ala Asp Cys
            180                 185                 190

Ser Asp Ala Asn Asp Ala Leu Ile Val Leu Ile His Leu Leu Met Leu
        195                 200                 205

Glu Ser Gly Tyr Ile Pro Gln Gly Thr Glu Ala Lys Ala Leu Ser Met
    210                 215                 220

Pro Glu Lys Trp Lys Leu Ser Gly Val Tyr Lys Leu Gln Tyr Met His
225                 230                 235                 240

Pro Leu Cys Glu Gly Ser Ser Ala Thr Leu Thr Cys Val Pro Leu Gly
                245                 250                 255

Asn Leu Ile Val Val Asn Ala Thr Leu Lys Ile Asn Asn Glu Ile Arg
            260                 265                 270

Ser Val Lys Arg Leu Gln Leu Leu Pro Lys Ser Phe Ile Cys Lys Glu
        275                 280                 285

Lys Leu Gly Glu Asn Val Ala Asn Ile Tyr Lys Asp Leu Gln Lys Leu
```

```
            290                 295                 300
Ser Arg Leu Phe Lys Asp Gln Leu Val Tyr Pro Leu Leu Ala Phe Thr
305                 310                 315                 320

Arg Gln Ala Leu Asn Leu Pro Asp Val Phe Gly Leu Val Val Leu Pro
                325                 330                 335

Leu Glu Leu Lys Leu Arg Ile Phe Arg Leu Leu Asp Val Arg Ser Val
            340                 345                 350

Leu Ser Leu Ser Ala Val Cys Arg Asp Leu Phe Thr Ala Ser Asn Asp
        355                 360                 365

Pro Leu Leu Trp Arg Phe Leu Tyr Leu Arg Asp Phe Arg Asp Asn Thr
370                 375                 380

Val Arg Val Gln Asp Thr Asp Trp Lys Glu Leu Tyr Arg Lys Arg His
385                 390                 395                 400

Ile Gln Arg Lys Glu Ser Pro Lys Gly Arg Phe Val Met Leu Leu Pro
                405                 410                 415

Ser Ser Thr His Thr Ile Pro Phe Tyr Pro Asn Pro Leu His Pro Arg
            420                 425                 430

Pro Phe Pro Ser Ser Arg Leu Pro Pro Gly Ile Ile Gly Gly Glu Tyr
        435                 440                 445

Asp Gln Arg Pro Thr Leu Pro Tyr Val Gly Asp Pro Ile Ser Ser Leu
450                 455                 460

Ile Pro Gly Pro Gly Glu Thr Pro Ser Gln Phe Pro Pro Leu Arg Pro
465                 470                 475                 480

Arg Phe Asp Pro Val Gly Pro Leu Pro Gly Pro Asn Pro Ile Leu Pro
                485                 490                 495

Gly Arg Gly Gly Pro Asn Asp Arg Phe Pro Phe Arg Pro Ser Arg Gly
            500                 505                 510

Arg Pro Thr Asp Gly Arg Leu Ser Phe Met
        515                 520
```

<210> SEQ ID NO 11
<211> LENGTH: 1075
<212> TYPE: DNA
<213> ORGANISM: Homo sapien
<220> FEATURE:
<221> NAME/KEY: CDS
<222> LOCATION: (52)...(1032)

<400> SEQUENCE: 11

```
gctaatttag ctttatttct tcttttagcc atcaagtttt atcgtagggc t atg caa        57
                                                          Met Gln
                                                            1 ctt gta cct gat ata gag ttc aag att act tat acc cgg tct cca gat       105
Leu Val Pro Asp Ile Glu Phe Lys Ile Thr Tyr Thr Arg Ser Pro Asp
        5                  10                  15 ggt gat ggc gtt gga aac agc tac att gaa gat aat gat gat gac agc       153
Gly Asp Gly Val Gly Asn Ser Tyr Ile Glu Asp Asn Asp Asp Asp Ser
 20                  25                  30 aaa atg gca gat ctc ttg tcc tac ttc cag cag caa ctc aca ttt cag       201
Lys Met Ala Asp Leu Leu Ser Tyr Phe Gln Gln Gln Leu Thr Phe Gln
 35                  40                  45                  50 gag tct gtg ctt aaa ctg tgt cag cct gag ctt gag agc agt cag att       249
Glu Ser Val Leu Lys Leu Cys Gln Pro Glu Leu Glu Ser Ser Gln Ile
                55                  60                  65 cac ata tca gtg ctg cca atg gag gtc ctg atg tac atc ttc cga tgg       297
His Ile Ser Val Leu Pro Met Glu Val Leu Met Tyr Ile Phe Arg Trp
            70                  75                  80
```

-continued

| | | |
|---|---|---|
| gtg gtg tct agt gac ttg gac ctc aga tca ttg gag cag ttg tcg ctg<br>Val Val Ser Ser Asp Leu Asp Leu Arg Ser Leu Glu Gln Leu Ser Leu<br>                85                  90                  95 | 345 |
| gtg tgc aga gga ttc tac atc tgt gcc aga gac cct gaa ata tgg cgt<br>Val Cys Arg Gly Phe Tyr Ile Cys Ala Arg Asp Pro Glu Ile Trp Arg<br>            100                 105                 110 | 393 |
| ctg gcc tgc ttg aaa gtt tgg ggc aga agc tgt att aaa ctt gtt ccg<br>Leu Ala Cys Leu Lys Val Trp Gly Arg Ser Cys Ile Lys Leu Val Pro<br>115                 120                 125                 130 | 441 |
| tac acg tcc tgg aga gag atg ttt tta gaa cgg cct cgt gtt cgg ttt<br>Tyr Thr Ser Trp Arg Glu Met Phe Leu Glu Arg Pro Arg Val Arg Phe<br>                135                 140                 145 | 489 |
| gat ggc gtg tat atc agt aaa acc aca tat att cgt caa ggg gaa cag<br>Asp Gly Val Tyr Ile Ser Lys Thr Thr Tyr Ile Arg Gln Gly Glu Gln<br>            150                 155                 160 | 537 |
| tct ctt gat ggt ttc tat aga gcc tgg cac caa gtg gaa tat tac agg<br>Ser Leu Asp Gly Phe Tyr Arg Ala Trp His Gln Val Glu Tyr Tyr Arg<br>            165                 170                 175 | 585 |
| tac ata aga ttc ttt cct gat ggc cat gtg atg atg ttg aca acc cct<br>Tyr Ile Arg Phe Phe Pro Asp Gly His Val Met Met Leu Thr Thr Pro<br>180                 185                 190 | 633 |
| gaa gag cct cag tcc att gtt cca cgt tta aga act agg aat acc agg<br>Glu Glu Pro Gln Ser Ile Val Pro Arg Leu Arg Thr Arg Asn Thr Arg<br>195                 200                 205                 210 | 681 |
| act gat gca att cta ctg ggt cac tat cgc ttg tca caa gac aca gac<br>Thr Asp Ala Ile Leu Leu Gly His Tyr Arg Leu Ser Gln Asp Thr Asp<br>                215                 220                 225 | 729 |
| aat cag acc aaa gta ttt gct gta ata act aag aaa aaa gaa gaa aaa<br>Asn Gln Thr Lys Val Phe Ala Val Ile Thr Lys Lys Lys Glu Glu Lys<br>            230                 235                 240 | 777 |
| cca ctt gac tat aaa tac aga tat ttt cgt cgt gtc cct gta caa gaa<br>Pro Leu Asp Tyr Lys Tyr Arg Tyr Phe Arg Arg Val Pro Val Gln Glu<br>            245                 250                 255 | 825 |
| gca gat cag agt ttt cat gtg ggg cta cag cta tgt tcc agt ggt cac<br>Ala Asp Gln Ser Phe His Val Gly Leu Gln Leu Cys Ser Ser Gly His<br>260                 265                 270 | 873 |
| cag agg ttc aac aaa ctc atc tgg ata cat cat tct tgt cac att act<br>Gln Arg Phe Asn Lys Leu Ile Trp Ile His His Ser Cys His Ile Thr<br>275                 280                 285                 290 | 921 |
| tac aaa tca act ggt gag act gca gtc agt gct ttt gag att gac aag<br>Tyr Lys Ser Thr Gly Glu Thr Ala Val Ser Ala Phe Glu Ile Asp Lys<br>                295                 300                 305 | 969 |
| atg tac acc ccc ttg ttc ttc gcc aga gta agg agc tac aca gct ttc<br>Met Tyr Thr Pro Leu Phe Phe Ala Arg Val Arg Ser Tyr Thr Ala Phe<br>            310                 315                 320 | 1017 |
| tca gaa agg cct ctg tagagcctca agtccagtcc tctatcactt ttgcatgaat<br>Ser Glu Arg Pro Leu<br>            325 | 1072 |
| taa | 1075 |

<210> SEQ ID NO 12
<211> LENGTH: 327
<212> TYPE: PRT
<213> ORGANISM: Homo sapien

<400> SEQUENCE: 12

Met Gln Leu Val Pro Asp Ile Glu Phe Lys Ile Thr Tyr Thr Arg Ser
 1               5                  10                  15

Pro Asp Gly Asp Gly Val Gly Asn Ser Tyr Ile Glu Asp Asn Asp Asp
            20                  25                  30

-continued

```
Asp Ser Lys Met Ala Asp Leu Leu Ser Tyr Phe Gln Gln Gln Leu Thr
        35                  40                  45
Phe Gln Glu Ser Val Leu Lys Leu Cys Gln Pro Glu Leu Glu Ser Ser
 50                  55                  60
Gln Ile His Ile Ser Val Leu Pro Met Glu Val Leu Met Tyr Ile Phe
 65                  70                  75                  80
Arg Trp Val Val Ser Asp Leu Asp Leu Arg Ser Leu Glu Gln Leu
                 85                  90                  95
Ser Leu Val Cys Arg Gly Phe Tyr Ile Cys Ala Arg Asp Pro Glu Ile
                100                 105                 110
Trp Arg Leu Ala Cys Leu Lys Val Trp Gly Arg Ser Cys Ile Lys Leu
            115                 120                 125
Val Pro Tyr Thr Ser Trp Arg Glu Met Phe Leu Glu Arg Pro Arg Val
130                 135                 140
Arg Phe Asp Gly Val Tyr Ile Ser Lys Thr Thr Tyr Ile Arg Gln Gly
145                 150                 155                 160
Glu Gln Ser Leu Asp Gly Phe Tyr Arg Ala Trp His Gln Val Glu Tyr
                165                 170                 175
Tyr Arg Tyr Ile Arg Phe Phe Pro Asp Gly His Val Met Met Leu Thr
                180                 185                 190
Thr Pro Glu Glu Pro Gln Ser Ile Val Pro Arg Leu Arg Thr Arg Asn
            195                 200                 205
Thr Arg Thr Asp Ala Ile Leu Leu Gly His Tyr Arg Leu Ser Gln Asp
            210                 215                 220
Thr Asp Asn Gln Thr Lys Val Phe Ala Val Ile Thr Lys Lys Lys Glu
225                 230                 235                 240
Glu Lys Pro Leu Asp Tyr Lys Tyr Arg Tyr Phe Arg Arg Val Pro Val
                245                 250                 255
Gln Glu Ala Asp Gln Ser Phe His Val Gly Leu Gln Leu Cys Ser Ser
                260                 265                 270
Gly His Gln Arg Phe Asn Lys Leu Ile Trp Ile His His Ser Cys His
            275                 280                 285
Ile Thr Tyr Lys Ser Thr Gly Glu Thr Ala Val Ser Ala Phe Glu Ile
            290                 295                 300
Asp Lys Met Tyr Thr Pro Leu Phe Phe Ala Arg Val Arg Ser Tyr Thr
305                 310                 315                 320
Ala Phe Ser Glu Arg Pro Leu
                325

<210> SEQ ID NO 13
<211> LENGTH: 2037
<212> TYPE: DNA
<213> ORGANISM: Homo sapien
<220> FEATURE:
<221> NAME/KEY: CDS
<222> LOCATION: (70)...(1410)

<400> SEQUENCE: 13
aagcaggcag gttgctcagc tgcccccgga gcggttcctc cacctgaggc agactccacg      60 tcggctggc atg agc cgg cgc ccc tgc agc tgc gcc cta cgg cca ccc cgc    111
           Met Ser Arg Arg Pro Cys Ser Cys Ala Leu Arg Pro Pro Arg
             1               5                  10 tgc tcc tgc agc gcc agc ccc agc gca gtg aca gcc gcc ggg cgc cct     159
Cys Ser Cys Ser Ala Ser Pro Ser Ala Val Thr Ala Ala Gly Arg Pro
 15                  20                  25                  30
```

-continued

| | | |
|---|---|---|
| cga ccc tcg gat agt tgt aaa gaa gaa agt tct acc ctt tct gtc aaa<br>Arg Pro Ser Asp Ser Cys Lys Glu Glu Ser Ser Thr Leu Ser Val Lys<br>35 40 45 | 207 | |
| atg aag tgt gat ttt aat tgt aac cat gtt cat tcc gga ctt aaa ctg<br>Met Lys Cys Asp Phe Asn Cys Asn His Val His Ser Gly Leu Lys Leu<br>50 55 60 | 255 | |
| gta aaa cct gat gac att gga aga cta gtt tcc tac acc cct gca tat<br>Val Lys Pro Asp Asp Ile Gly Arg Leu Val Ser Tyr Thr Pro Ala Tyr<br>65 70 75 | 303 | |
| ttg gaa ggt tcc tgt aaa gac tgc att aaa gac tat gaa agg ctg tca<br>Leu Glu Gly Ser Cys Lys Asp Cys Ile Lys Asp Tyr Glu Arg Leu Ser<br>80 85 90 | 351 | |
| tgt att ggg tca ccg att gtg agc cct agg att gta aaa ctt gaa act<br>Cys Ile Gly Ser Pro Ile Val Ser Pro Arg Ile Val Lys Leu Glu Thr<br>95 100 105 110 | 399 | |
| gaa agc aag cgc ttg cat aac aag gaa aat caa cat gtg caa cag aca<br>Glu Ser Lys Arg Leu His Asn Lys Glu Asn Gln His Val Gln Gln Thr<br>115 120 125 | 447 | |
| ctt aat agt aca aat gaa ata gaa gca cta gag acc agt aga ctt tat<br>Leu Asn Ser Thr Asn Glu Ile Glu Ala Leu Glu Thr Ser Arg Leu Tyr<br>130 135 140 | 495 | |
| gaa gac agt ggc tat tcc tca ttt tct cta caa agt ggc ctc agt gaa<br>Glu Asp Ser Gly Tyr Ser Ser Phe Ser Leu Gln Ser Gly Leu Ser Glu<br>145 150 155 | 543 | |
| cat gaa gaa ggt acc ctc ctg gag gag aat ttc ggt gac agt cta caa<br>His Glu Glu Gly Thr Leu Leu Glu Glu Asn Phe Gly Asp Ser Leu Gln<br>160 165 170 | 591 | |
| tcc tgc ctg cta caa ata caa agc cca gac caa tat ccc aac aaa aac<br>Ser Cys Leu Leu Gln Ile Gln Ser Pro Asp Gln Tyr Pro Asn Lys Asn<br>175 180 185 190 | 639 | |
| ttg ctg cca gtt ctt cat ttt gaa aaa gtg gtt tgt tca aca tta aaa<br>Leu Leu Pro Val Leu His Phe Glu Lys Val Val Cys Ser Thr Leu Lys<br>195 200 205 | 687 | |
| aag aat gca aaa cga aat cct aaa gta gat cgg gag atg ctg aag gaa<br>Lys Asn Ala Lys Arg Asn Pro Lys Val Asp Arg Glu Met Leu Lys Glu<br>210 215 220 | 735 | |
| att ata gcc aga gga aat ttt aga ctg cag aat ata att ggc aga aaa<br>Ile Ile Ala Arg Gly Asn Phe Arg Leu Gln Asn Ile Ile Gly Arg Lys<br>225 230 235 | 783 | |
| atg ggc cta gaa tgt gta gat att ctc agc gaa ctc ttt cga agg gga<br>Met Gly Leu Glu Cys Val Asp Ile Leu Ser Glu Leu Phe Arg Arg Gly<br>240 245 250 | 831 | |
| ctc aga cat gtc tta gca act att tta gca caa ctc agt gac atg gac<br>Leu Arg His Val Leu Ala Thr Ile Leu Ala Gln Leu Ser Asp Met Asp<br>255 260 265 270 | 879 | |
| tta atc aat gtg tct aaa gtg agc aca act tgg aag aag atc cta gaa<br>Leu Ile Asn Val Ser Lys Val Ser Thr Thr Trp Lys Lys Ile Leu Glu<br>275 280 285 | 927 | |
| gat gat aag ggg gca ttc cag ttg tac agt aaa gca ata caa aga gtt<br>Asp Asp Lys Gly Ala Phe Gln Leu Tyr Ser Lys Ala Ile Gln Arg Val<br>290 295 300 | 975 | |
| acc gaa aac aac aat aaa ttt tca cct cat gct tca acc aga gaa tat<br>Thr Glu Asn Asn Asn Lys Phe Ser Pro His Ala Ser Thr Arg Glu Tyr<br>305 310 315 | 1023 | |
| gtt atg ttc aga acc cca ctg gct tct gtt cag aaa tca gca gcc cag<br>Val Met Phe Arg Thr Pro Leu Ala Ser Val Gln Lys Ser Ala Ala Gln<br>320 325 330 | 1071 | |
| act tct ctc aaa aaa gat gct caa acc aag tta tcc aat caa ggt gat<br>Thr Ser Leu Lys Lys Asp Ala Gln Thr Lys Leu Ser Asn Gln Gly Asp<br>335 340 345 350 | 1119 | |

```
cag aaa ggt tct act tat agt cga cac aat gaa ttc tct gag gtt gcc    1167
Gln Lys Gly Ser Thr Tyr Ser Arg His Asn Glu Phe Ser Glu Val Ala
            355                 360                 365 aag aca ttg aaa aag aac gaa agc ctc aaa gcc tgt att cgc tgt aat    1215
Lys Thr Leu Lys Lys Asn Glu Ser Leu Lys Ala Cys Ile Arg Cys Asn
        370                 375                 380 tca cct gca aaa tat gat tgc tat tta caa cgg gca acc tgc aaa cga    1263
Ser Pro Ala Lys Tyr Asp Cys Tyr Leu Gln Arg Ala Thr Cys Lys Arg
            385                 390                 395 gaa ggc tgt gga ttt gat tat tgt acg aag tgt ctc tgt aat tat cat    1311
Glu Gly Cys Gly Phe Asp Tyr Cys Thr Lys Cys Leu Cys Asn Tyr His
    400                 405                 410 act act aaa gac tgt tca gat ggc aag ctc ctc aaa gcc agt tgt aaa    1359
Thr Thr Lys Asp Cys Ser Asp Gly Lys Leu Leu Lys Ala Ser Cys Lys
415                 420                 425                 430 ata ggt ccc ctg cct ggt aca aag aaa agc aaa aag aat tta cga aga    1407
Ile Gly Pro Leu Pro Gly Thr Lys Lys Ser Lys Lys Asn Leu Arg Arg
                435                 440                 445 ttg tgatctctta ttaaatcaat tgttactgat catgaatgtt agttagaaaa          1460
Leu tgttaggttt taacttaaaa aaaattgtat tgtgattttc aatttatgt tgaaatcggt    1520
gtagtatcct gaggttttt tccccccaga agataaagag gatagacaac ctcttaaaat    1580
attttacaa tttaatgaga aaagtttaa aattctcaat acaaatcaaa caatttaaat     1640
attttaagaa aaaggaaaa gtagatagtg atactgaggg taaaaaaaaa ttgattcaat    1700
tttatggtaa aggaaaccca tgcaatttta cctagacagt cttaaatatg tctggttttc   1760
catctgttag catttcagac attttatgtt cctcttactc aattgatacc aacagaaata   1820
tcaacttctg gagtctatta aatgtgttgt cacctttcta aagcttttt tcattgtgtg    1880
tatttcccaa gaaagtatcc tttgtaaaaa cttgcttgtt ttccttattt ctgaaatctg   1940
ttttaatatt tttgtataca tgtaaatatt tctgtatttt ttatatgtca agaatatgt    2000
ctcttgtatg tacatataaa aataaatttt gctcaat                            2037
```

<210> SEQ ID NO 14
<211> LENGTH: 447
<212> TYPE: PRT
<213> ORGANISM: Homo sapien

<400> SEQUENCE: 14

```
Met Ser Arg Arg Pro Cys Ser Cys Ala Leu Arg Pro Pro Arg Cys Ser
1               5                   10                  15

Cys Ser Ala Ser Pro Ser Ala Val Thr Ala Ala Gly Arg Pro Arg Pro
            20                  25                  30

Ser Asp Ser Cys Lys Glu Glu Ser Ser Thr Leu Ser Val Lys Met Lys
        35                  40                  45

Cys Asp Phe Asn Cys Asn His Val His Ser Gly Leu Lys Leu Val Lys
    50                  55                  60

Pro Asp Asp Ile Gly Arg Leu Val Ser Tyr Thr Pro Ala Tyr Leu Glu
65                  70                  75                  80

Gly Ser Cys Lys Asp Cys Ile Lys Asp Tyr Glu Arg Leu Ser Cys Ile
                85                  90                  95

Gly Ser Pro Ile Val Ser Pro Arg Ile Val Lys Leu Glu Thr Glu Ser
            100                 105                 110

Lys Arg Leu His Asn Lys Glu Asn Gln His Val Gln Thr Leu Asn
        115                 120                 125
```

-continued

```
Ser Thr Asn Glu Ile Glu Ala Leu Glu Thr Ser Arg Leu Tyr Glu Asp
    130                 135                 140

Ser Gly Tyr Ser Ser Phe Ser Leu Gln Ser Gly Leu Ser Glu His Glu
145                 150                 155                 160

Glu Gly Thr Leu Leu Glu Glu Asn Phe Gly Asp Ser Leu Gln Ser Cys
                165                 170                 175

Leu Leu Gln Ile Gln Ser Pro Asp Gln Tyr Pro Asn Lys Asn Leu Leu
            180                 185                 190

Pro Val Leu His Phe Glu Lys Val Val Cys Ser Thr Leu Lys Lys Asn
        195                 200                 205

Ala Lys Arg Asn Pro Lys Val Asp Arg Glu Met Leu Lys Glu Ile Ile
    210                 215                 220

Ala Arg Gly Asn Phe Arg Leu Gln Asn Ile Ile Gly Arg Lys Met Gly
225                 230                 235                 240

Leu Glu Cys Val Asp Ile Leu Ser Glu Leu Phe Arg Arg Gly Leu Arg
                245                 250                 255

His Val Leu Ala Thr Ile Leu Ala Gln Leu Ser Asp Met Asp Leu Ile
            260                 265                 270

Asn Val Ser Lys Val Ser Thr Thr Trp Lys Lys Ile Leu Glu Asp Asp
        275                 280                 285

Lys Gly Ala Phe Gln Leu Tyr Ser Lys Ala Ile Gln Arg Val Thr Glu
    290                 295                 300

Asn Asn Asn Lys Phe Ser Pro His Ala Ser Thr Arg Glu Tyr Val Met
305                 310                 315                 320

Phe Arg Thr Pro Leu Ala Ser Val Gln Lys Ser Ala Ala Gln Thr Ser
                325                 330                 335

Leu Lys Lys Asp Ala Gln Thr Lys Leu Ser Asn Gln Gly Asp Gln Lys
            340                 345                 350

Gly Ser Thr Tyr Ser Arg His Asn Glu Phe Ser Glu Val Ala Lys Thr
        355                 360                 365

Leu Lys Lys Asn Glu Ser Leu Lys Ala Cys Ile Arg Cys Asn Ser Pro
    370                 375                 380

Ala Lys Tyr Asp Cys Tyr Leu Gln Arg Ala Thr Cys Lys Arg Glu Gly
385                 390                 395                 400

Cys Gly Phe Asp Tyr Cys Thr Lys Cys Leu Cys Asn Tyr His Thr Thr
                405                 410                 415

Lys Asp Cys Ser Asp Gly Lys Leu Leu Lys Ala Ser Cys Lys Ile Gly
            420                 425                 430

Pro Leu Pro Gly Thr Lys Lys Ser Lys Lys Asn Leu Arg Arg Leu
        435                 440                 445

<210> SEQ ID NO 15
<211> LENGTH: 20
<212> TYPE: PRT
<213> ORGANISM: Homo sapien

<400> SEQUENCE: 15

Ser Glu Ser Pro Gly Ala Leu Arg Ser Gly Ser Leu Arg Cys Ile Ser
1               5                   10                  15

Leu Arg Ile Cys
            20

<210> SEQ ID NO 16
<211> LENGTH: 20
<212> TYPE: PRT
```

-continued

<213> ORGANISM: Homo sapien

<400> SEQUENCE: 16

Val Cys Arg Gly Arg Ile Arg Ser Gly Ser Leu Arg Cys Ile Ser Leu
1               5                   10                  15

Arg Ile Cys Arg
            20

<210> SEQ ID NO 17
<211> LENGTH: 20
<212> TYPE: PRT
<213> ORGANISM: Homo sapien

<400> SEQUENCE: 17

Leu Leu Arg Leu Gly Cys Ile Arg Leu Leu Met Leu Arg Arg Gly Val
1               5                   10                  15

Val Phe Arg Leu
            20

<210> SEQ ID NO 18
<211> LENGTH: 20
<212> TYPE: PRT
<213> ORGANISM: Homo sapien

<400> SEQUENCE: 18

Val Leu Phe Leu Ser Leu Arg Phe Trp Gly Leu Asn Ile Val Val Met
1               5                   10                  15

Gly Arg Leu Leu
            20

<210> SEQ ID NO 19
<211> LENGTH: 20
<212> TYPE: PRT
<213> ORGANISM: Homo sapien

<400> SEQUENCE: 19

Cys Arg Ser Leu Gly Val Ile Val Gly Gly Thr Glu Ala Ala Gly Ala
1               5                   10                  15

Pro Thr Phe Ile
            20

<210> SEQ ID NO 20
<211> LENGTH: 20
<212> TYPE: PRT
<213> ORGANISM: Homo sapien

<400> SEQUENCE: 20

Val Leu Phe Leu Ser Leu Arg Phe Trp Gly Leu Asn Ile Val Val Met
1               5                   10                  15

Gly Arg Leu Leu
            20

<210> SEQ ID NO 21
<211> LENGTH: 20
<212> TYPE: PRT
<213> ORGANISM: Homo sapien

<400> SEQUENCE: 21

Trp Leu Arg Arg Gly Leu Val Gly Val Phe Phe Leu Leu Ser Arg Val
1               5                   10                  15

Met Val Gly Ile
            20

<210> SEQ ID NO 22
<211> LENGTH: 20
<212> TYPE: PRT
<213> ORGANISM: Homo sapien

<400> SEQUENCE: 22

Ser Leu Gly Leu Ser Val Cys Ile Gly Arg Arg Ala Gly Gly Gly Phe
 1               5                  10                  15

Arg Gly Phe Gly
            20

<210> SEQ ID NO 23
<211> LENGTH: 20
<212> TYPE: PRT
<213> ORGANISM: Homo sapien

<400> SEQUENCE: 23

Arg Phe Ala Leu Ser Ile Gly Val Cys Val Val Arg Val Gly Ile
 1               5                  10                  15

Cys Leu Gly Met
            20

<210> SEQ ID NO 24
<211> LENGTH: 20
<212> TYPE: PRT
<213> ORGANISM: Homo sapien

<400> SEQUENCE: 24

Ser Ala Val Leu Val Leu Val Tyr Val Ser Ala Ala Leu Arg Gly Arg
 1               5                  10                  15

Gly Phe Gly Ile
            20

<210> SEQ ID NO 25
<211> LENGTH: 20
<212> TYPE: PRT
<213> ORGANISM: Homo sapien

<400> SEQUENCE: 25

His Gly Gly Gly Arg Gly Ala Leu Val Ser Val Met Tyr Leu Cys Gly
 1               5                  10                  15

Phe Ile Arg Leu
            20

<210> SEQ ID NO 26
<211> LENGTH: 18
<212> TYPE: PRT
<213> ORGANISM: Homo sapien

<400> SEQUENCE: 26

Arg Gly Arg Val Ile Gly Met Trp Val Gly Leu Arg Cys Arg Met Phe
 1               5                  10                  15

Leu Val

<210> SEQ ID NO 27
<211> LENGTH: 15
<212> TYPE: PRT
<213> ORGANISM: Homo sapien

<400> SEQUENCE: 27

Val Asp Trp Ala Val Tyr Ser Val Val Trp Arg Tyr Thr Thr Thr

```
        1               5              10              15
```

<210> SEQ ID NO 28
<211> LENGTH: 20
<212> TYPE: PRT
<213> ORGANISM: Homo sapien

<400> SEQUENCE: 28

```
Lys Thr Ser Val Ile Leu Val Trp Arg Leu Ser Leu Phe Phe Cys Leu
 1               5                  10                  15

Tyr Arg Ser Leu
            20
```

<210> SEQ ID NO 29
<211> LENGTH: 7
<212> TYPE: PRT
<213> ORGANISM: Homo sapien

<400> SEQUENCE: 29

```
Ala Asn Arg Cys Trp Arg Glu
 1               5
```

<210> SEQ ID NO 30
<211> LENGTH: 13
<212> TYPE: PRT
<213> ORGANISM: Homo sapien

<400> SEQUENCE: 30

```
Glu Gly Thr Leu Ser Lys Arg Met Trp Arg Thr His Asn
 1               5                  10
```

<210> SEQ ID NO 31
<211> LENGTH: 10
<212> TYPE: PRT
<213> ORGANISM: Homo sapien

<400> SEQUENCE: 31

```
Ser Trp Arg Asp Met Thr Gln Ser Gly Met
 1               5                  10
```

<210> SEQ ID NO 32
<211> LENGTH: 11
<212> TYPE: PRT
<213> ORGANISM: Homo sapien

<400> SEQUENCE: 32

```
Asp Val Pro Trp Gln Arg Ala Cys Ala Arg Gln
 1               5                  10
```

<210> SEQ ID NO 33
<211> LENGTH: 9
<212> TYPE: PRT
<213> ORGANISM: Homo sapien

<400> SEQUENCE: 33

```
Leu Glu Arg Val Ala Arg Trp Val Leu
 1               5
```

<210> SEQ ID NO 34
<211> LENGTH: 12
<212> TYPE: PRT
<213> ORGANISM: Homo sapien

<400> SEQUENCE: 34

```
Val Ala Asp Val Leu Val Phe Trp Gly Tyr Val Phe
1               5                   10
```

<210> SEQ ID NO 35
<211> LENGTH: 8
<212> TYPE: PRT
<213> ORGANISM: Homo sapien

<400> SEQUENCE: 35

```
Gly Asp Val Gly Val Phe Pro Glu
1               5
```

<210> SEQ ID NO 36
<211> LENGTH: 16
<212> TYPE: PRT
<213> ORGANISM: Homo sapien
<220> FEATURE:
<221> NAME/KEY: VARIANT
<222> LOCATION: (1)...(16)
<223> OTHER INFORMATION: Xaa = Any Amino Acid

<400> SEQUENCE: 36

```
Pro Glu Met Met Leu Glu Gly Pro Lys Tyr Cys Leu Xaa Leu Xaa Glu
1               5                   10                  15
```

<210> SEQ ID NO 37
<211> LENGTH: 7
<212> TYPE: PRT
<213> ORGANISM: Homo sapien

<400> SEQUENCE: 37

```
Leu Leu Tyr Gly Ala Leu Ala
1               5
```

<210> SEQ ID NO 38
<211> LENGTH: 11
<212> TYPE: PRT
<213> ORGANISM: Homo sapien

<400> SEQUENCE: 38

```
Gly Ala Ile Lys Phe Ala His Glu Ser Cys Glu
1               5                   10
```

<210> SEQ ID NO 39
<211> LENGTH: 5
<212> TYPE: PRT
<213> ORGANISM: Homo sapien

<400> SEQUENCE: 39

```
Pro Met Ala Met Asp
1               5
```

<210> SEQ ID NO 40
<211> LENGTH: 5
<212> TYPE: PRT
<213> ORGANISM: Homo sapien

<400> SEQUENCE: 40

```
Gln Glu Glu Glu Met
1               5
```

<210> SEQ ID NO 41
<211> LENGTH: 12
<212> TYPE: PRT
<213> ORGANISM: Homo sapien

-continued

```
<400> SEQUENCE: 41

Ile Ser Val Val His Gly Ile Gly Ser Asp Ser Asp
  1               5                  10

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
gggaattcgg acttatggca tgtaaaca                                    28

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
tagccaagtt gcgaatgga                                              19

<210> SEQ ID NO 44
<211> LENGTH: 35
<212> TYPE: DNA
<213> ORGANISM: Artificial Sequence
<220> FEATURE:
<223> OTHER INFORMATION: Primer

<400> SEQUENCE: 44
gtgaattcat gcaacttgta cctgatatag agttc                            35

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
ggactcgagg ctctacagag gcc                                         23

<210> SEQ ID NO 46
<211> LENGTH: 31
<212> TYPE: DNA
<213> ORGANISM: Artificial Sequence
<220> FEATURE:
<223> OTHER INFORMATION: Primer

<400> SEQUENCE: 46
gatcaagctt atggcttcag aagagctaca g                                31

<210> SEQ ID NO 47
<211> LENGTH: 37
<212> TYPE: DNA
<213> ORGANISM: Artificial Sequence
<220> FEATURE:
<223> OTHER INFORMATION: Primer

<400> SEQUENCE: 47
gatcgaattc tccaaattcc gtgtctcctt tggcttg                          37

<210> SEQ ID NO 48
```

```
<211> LENGTH: 36
<212> TYPE: DNA
<213> ORGANISM: Artificial Sequence
<220> FEATURE:
<223> OTHER INFORMATION: Primer

<400> SEQUENCE: 48
cctctgaatt ccatatgagc gataaaatta ttcacc                              36

<210> SEQ ID NO 49
<211> LENGTH: 34
<212> TYPE: DNA
<213> ORGANISM: Artificial Sequence
<220> FEATURE:
<223> OTHER INFORMATION: Primer

<400> SEQUENCE: 49
gatcctcgag tagatggcca gctaggccag gtta                                34
```